United States Patent [19]

Matsumoto et al.

[11] Patent Number: 4,977,170
[45] Date of Patent: Dec. 11, 1990

[54] ISOPRENOIDAMINE COMPOUNDS WHICH ARE USEFUL ANTIULCER AGENTS

[75] Inventors: Saichi Matsumoto; Masami Doteuchi, both of Osaka; Takuji Mizui, Hyogo; Kentaro Hirai, Kyoto, all of Japan

[73] Assignee: Shionogi & Co., Ltd., Osaka, Japan

[21] Appl. No.: 346,898

[22] Filed: May 3, 1989

Related U.S. Application Data

[62] Division of Ser. No. 837,192, Mar. 10, 1986, Pat. No. 4,900,749.

[30] Foreign Application Priority Data

Mar. 15, 1985 [JP] Japan ................................. 60-52970

[51] Int. Cl.$^5$ .................... C07D 213/72; A61K 31/44
[52] U.S. Cl. .................................. 514/352; 514/237.8; 514/456; 514/585; 514/586; 514/587; 514/595; 514/596; 514/597; 514/598; 514/357; 544/162; 546/336; 549/366; 564/26; 564/29; 564/30; 564/47; 564/54; 564/59; 564/53
[58] Field of Search ...................... 564/26, 29, 30, 47, 564/53, 54, 59; 544/162; 546/336; 549/366; 514/237.8, 352, 357, 456, 585, 586, 587, 595, 596, 597, 598

[56] References Cited

U.S. PATENT DOCUMENTS 3,400,132 9/1968 Horrom et al. ..................... 546/336
3,884,941 5/1975 Karrer ................................. 549/553
4,151,357 4/1979 Mishima et al. .................... 544/391
4,521,417 6/1985 Nakamoto et al. ................. 514/255

FOREIGN PATENT DOCUMENTS 183757 11/1982 Japan ................................... 548/400
938712 10/1963 United Kingdom ................ 560/8

OTHER PUBLICATIONS

Eichholzer et al., Photochemistry, vol. 21, No. 1, 1982, pp. 97–99.
Nagashima et al., Journal of the Chemical Society, Chemical Communications, 1984, pp. 652–653.
Overman, Journal of the American Chemical Society, vol. 98, No. 10, 1976, pp. 2901–2910.
Chemical Abstracts, vol. 106, No. 5, Abstract 33356f, Yamatsu et al., p. 581, Feb. 2, 1987.

Primary Examiner—John M. Ford
Assistant Examiner—Zinna Northington-Davis
Attorney, Agent, or Firm—Birch, Stewart, Kolasch & Birch

[57] ABSTRACT

Novel isoprenoidamine compounds (I) which show antiulcer activity are provided.

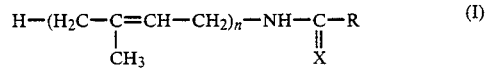

16 Claims, No Drawings

ISOPRENOIDAMINE COMPOUNDS WHICH ARE USEFUL ANTIULCER AGENTS

This application is a divisional of copending application Ser. No. 06/837,192, filed on Mar. 10, 1986 now U.S. Pat. No. 4,900,749.

BACKGROUND OF THE INVENTION

1. Field of the Invention

The present invention relates to novel isoprenoidamine derivatives which show antiulcer activity.

2. Prior Art

Gefarnate [GB Pat. No. 938712] has been commercially available as an isoprenoid derivative which has antiulcer activity and geranylgeranyl acetone [JPN Unexamd. Pat. Publn. No. 53-145922] has been developed, but these antiulcer activities are caused by cytoprotective actions.

Isoprenoids having cytoprotective actions such as N-methyl-N'-geranylgeranyl acetyl piperazine [JPN Unexamd. Pat. Publn. No. 59-1474] have also been developed.

BRIEF SUMMARY OF THE INVENTION

The present invention relates to isoprenoidamine derivatives(I):

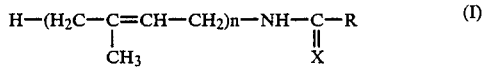

wherein n is an integer of 1 to 6; R is (i) hydrogen, (ii) $C_1$–$C_{15}$ alkyl optionally substituted by a member selected from the group consisting of halogen, cyano, phenyl, $C_1$–$C_5$ alkyl-phenyl, phenoxy, benzamido, di($C_1$–$C_5$ alkyl)amino, $C_1$–$C_5$ alkoxy, and 5-or 6- membered heterocyclic group, (iii) $C_2$–$C_5$ alkenyl optionally substituted by a member selected from the group consisting of phenyl and 5- or 6-membered heterocyclic group, (iv) $C_4$–$C_{12}$ alkadienyl, (v) aryl optionally substituted by a member selected from the group consisting of halogen, $C_1$–$C_5$ alkyl, $C_1$–$C_5$ alkoxy, $C_1$ –$C_5$ alkanoyloxy, di($C_1$–$C_5$ alkyl)amino, $C_2$–$C_6$ alkoxycarbonyl, $C_1$–$C_5$ alkylthio, $C_1$–$C_5$ alkylsufinyl, $C_1$–$C_5$ alkylsulfonyl, nitro, and hydroxy, (vi) amino optionally substituted by a member selected from the group consisting of di($C_1$–$C_5$ alkyl)amino-($C_1$–$C_5$ alkyl), phenyl($C_1$–$C_5$ alkyl), halogenophenyl($C_1$–$C_5$ alkyl), 3, 4-methylenedioxyphenyl($C_1$–$C_5$ alkyl), morpholinyl($C_1$–$C_5$ alkyl), pyridyl-$C_1$–$C_5$ alkyl, phenyl, halogenophenyl, trifluoromethylphenyl, $C_1$–$C_5$ alkoxy-phenyl, pyridyl, and $C_1$–$C_5$ alkyl, (vii) heterocyclic group optionally substituted by a member selected from the group consisting of $C_1$–$C_5$ alkyl, phenylamino, halogenophenylamino, trifluoromethylphenylamino, $C_1$–$C_5$ alkoxyphenylamino, $C_1$–$C_5$ alkoxy, $C_2$–$C_6$ alkoxycarbonyl, phenyl, pyridyl, halogenobenzoyl, halogenobenzyl, and methylenedioxyphenylmethyl; and X is sulfur or oxygen or acid addition salt thereof; an antiulcer composition comprising one or more said compounds and one or more carriers; and a complex comprising said compound and a cyclodextrin.

DETAILED DESCRIPTION OF THE INVENTION

The present invention relates to the compound of the formula:

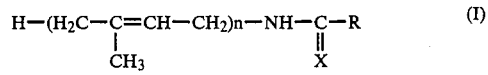

wherein n is an integer of 1 to 6; R is (i) hydrogen, (ii) $C_1$–$C_{15}$ alkyl optionally substituted by a member selected from the group consisting of halogen, cyano, phenyl, $C_1$–$C_5$ alkyl-phenyl, phenoxy, benzamido, di($C_1$–$C_5$ alkyl)amino, $C_1$–$C_5$ alkoxy, and 5-or 6- membered heterocyclic group, (iii) $C_2$–$C_5$ alkenyl optionally substituted by a member selected from the group consisting of phenyl and 5- or 6-membered heterocyclic group, (iv) $C_4$–$C_{12}$ alkadienyl, (v) aryl optionally substituted by a member selected from the group consisting of halogen, $C_1$–$C_5$ alkyl, $C_1$–$C_5$ alkoxy, $C_1$–$C_5$ alkanoyloxy, di($C_1$–$C_5$ alkyl)amino, $C_2$–$C_6$ alkoxycarbonyl, $C_1$–$C_5$ alkylthio, $C_1$–$C_5$ alkysulfinyl, $C_1$–$C_5$ alkylsulfonyl, nitro, and hydroxy, (vi) amino optionally substituted by a member selected from the group consisting of di($C_1$–$C_5$ alkyl)amino-($C_1$–$C_5$ alkyl), phenyl($C_1$–$C_5$ alkyl), halogenophenyl($C_1$–$C_5$ alkyl), 3, 4-methylenedioxyphenyl($C_1$–$C_5$ alkyl), morpholinyl($C_1$–$C_5$ alkyl), pyridyl-$C_1$–$C_5$ alkyl, phenyl, halogenophenyl, trifluoromethylphenyl, $C_1$–$C_5$ alkoxy-phenyl, pyridyl, and $C_1$–$C_5$ alkyl, (vii) heterocyclic group optionally substituted by a member selected from the group consisting of $C_1$– $C_5$ alkyl, phenylamino, halogenophenylamino, trifluoromethylphenylamino, $C_1$–$C_5$ alkoxyphenylamino, $C_1$–$C_5$ alkoxy, $C_2$–$C_6$ alkoxycarbonyl, phenyl, pyridyl, halogenobenzoyl, halogenobenzyl, and 3,4-methylenedioxyphenylmethyl; and X is sulfur or oxygen or acid addition salt thereof.

The meanings of the definition used above are explained below. The $C_1$–$C_{15}$ alkyl includes straight or branched chain $C_1$–$C_{15}$ alkyl, for example methyl, ethyl, propyl, butyl, pentyl, hexyl, heptyl, octyl, nonyl, decyl, undecyl, dodecyl, tridecyl, tetradecyl, pentadecyl, and the like. The $C_1$–$C_5$ alkyl is exemplified by methyl, ethyl, n-propyl, isopropyl, n-butyl, isobutyl, sec-butyl, tert-butyl, n-pentyl, isopentyl, sec-pentyl, neo-pentyl, tert-pentyl, and the like. The $C_1$–$C_5$ alkoxy means methoxy, ethoxy, n-propoxy, isopropoxy, n-butoxy, isobutoxy, sec-butoxy, tert-butoxy, n-pentyloxy, isopentyloxy, sec-pentyloxy, neo-pentyloxy, tert-pentyloxy, and the like. The $C_2$–$C_6$ alkenyl includes vinyl, 1-propenyl, 2-propenyl, isopropenyl, 2-butenyl, 2-pentenyl, 3-pentenyl, and the like. The $C_4$–$C_{12}$ alkadienyl includes 1,3-pentadienyl, isoprenyl, 1,3-hexadienyl, 4,8-dimethyl-3,7-nonadienyl, and the like. The $C_1$–$C_5$ alkanoyloxy includes formyloxy, acetyloxy, vareryloxy, pivaloyloxy, and the like. The $C_2$–$C_6$ alkoxycarbonyl is exemplified by methoxycarbonyl, ethoxycarbonyl, propoxycarbonyl, butoxycarbonyl, pentyloxycarbonyl, and the like. The $C_1$–$C_5$ alkylthio means mercapto substituted by $C_1$–$C_5$ alkyl. The $C_1$–$C_5$ alkylsulfinyl means sulfinyl substituted by $C_1$–$C_5$ alkyl. The $C_1$–$C_5$ alkylsulfonyl means sulfonyl substituted by $C_1$–$C_5$ alkyl. The halogen means fluorine, chlorine, bromine, and iodine. The aryl includes phenyl, naphthyl, and the like. The heterocyclic group includes unsaturated heterocyclic groups containing N, O, and/or S such as furyl, thienyl, pyrrolyl, imidazoly, pyrazolyl, pyridyl, pyrazinyl, pyrimidinyl, oxazolyl, isoxazolyl, thiazolyl, and indolyl; and saturated heterocyclic groups such as pyrrolidinyl, piperidinyl, piperazinyl, and morpholinyl. The 5- or 6- membered heterocyclic group means the above heterocyclic group except for indolyl.

Novel prenylamido group of the present compound (I) is characteristic; and the substituents R on the compound (I) should not be limited if "R" can be used to attain the purpose of the present invention. The substituents R described in the definitions are some of preferable examples.

The compounds (I) can be prepared by the following methods A, B, C, D, E, F, G, and/or H.

Method A

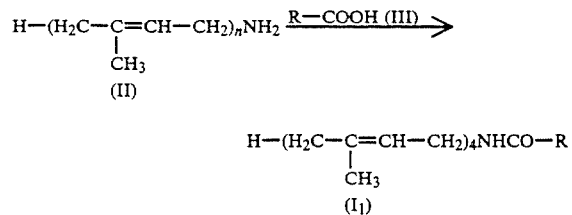

wherein n and R each has the same meaning as defined above; the carboxylic acid (III) can be a reactive derivative thereof.

In this method, a prenylamine (II) is subjected to amidation to give the objective isoprenoidamine derivative (I₁). The reaction conditions are illustratively explained below.

(a) Method using a carboxlic acid halide

A carboxlic acid halide is allowed to react with a prenylamine (II) in an appropriate solvent preferably in the presence of a base in this method.

As the carboxylic acid halide, carboxylic acid chloride, carboxylic acid bromide, etc. may be used. The acid halide can be provided from a carboxylic acid and a halogenating agent and, if necessary, isolated by purification.

Representatives of halogenating agents are thionyl chloride, phosphorus oxychloride, phosphorus pentachloride, phosphorus pentabromide, phosphorus oxbromide, triphenylphosphine tetratbromomethane, triphenylphosphine tetrachloromethane, and the like.

The reaction is carried out at a temperature of about $-50°$ to about $200°$ C., preferably about $-10°$ to about $100°$ C. and terminates within a period of several ten minutes to several ten hours.

(b) Method using dicyclohexylcarbodiimide (DCC)

A carboxylic acid (III) is condensed with a prenylamine (III) by dehydration.

(c) Method using carbonyl diimidazoles

An activated caroxylic acid (III) by the reaction of carbonyl diimidazole is condensed with a tetraprenylamine (II).

(d) Method using activated esters

An activated ester of carboxylic acid (III) such as p-nitrophenyl ester, N-hydroxysuccinimide ester, N-hydroxyphthalimide ester, or 1-methyl-2-pyridinium ester is allowed to react with a tetraprenylamine (II).

The reaction is carried out in an appropriate solvent preferably in the presence of a base at a temperature of about 0 to about 200° C., preferably from room temperature to a temperature under reflux, and terminates within a period of several ten minutes to several ten hours.

(e) Method using carboxylic acid ester

A prenylamine (II) is allowed to react with an ester derivative of carboxylic acid provided by the reaction of a carboxylic acid (III) with, for example, lower alkanols (e.g., methanol, ethanol, propanol, isopropanol, butanol, isobutanol, tert-butanol, etc.).

(f) Condensation of ortho-ester

A prenylamine (II) is allowed to react with trialkyl ortho-ester or dialkylaminodialkyl ortho-ester of carboxylic acid (III) and then the product is hydrolyzed by an acid or a base. In particular, when "R" on the objective compound (I₁) is hydrogen, the prenylamine (II) is preferably reacted with trialkyl orthoformate or dialkylaminodialkyl orthoformate.

The reaction is carried out in an appropriate solvent preferably in the presence of a base from room temperature to under a reflux temperature, and terminates within a period of several ten minutes to several hours.

(g) Mixed acid anhydride method

A mixed acid anhydride provided by the reaction of the carboxylic acid with a carboxylic acid halide is allowed to react with a tetraprenylamine (II) to give the compound (I₁).

The carboxylic acid halide includes methyl chloroformate, ethyl chloroformate, isopropyl chloroformate, methyl bromoformate, ethyl bromoformate, pivaloyl chloride, etc.

The reaction is preferably carried out in an appropriate solvent in the presence of a base at a temperature of about $-50°$ to about $100°$ C.

(h) Carboxylic acid anhydride method

A carboxylic acid (III) is allowed to react with a dehydrating agent to produce a carboxylic acid anhydride. The carboxylic acid anhydride is allowed to react with a prenylamine (II).

(i) Oxidation-reduction condensing method

A carboxylic acid (III) is condensed with a prenylamine (II) in the presence of 2-pyridyl disulfide and triphenylphosphine.

In the above methods, as the solvent halogenohydrocarbons (e.g. dichloromethane, dichloroethane, chloroform, tetrachloroethane, etc.); ethers (e.g. diethyl ether, diisopropyl ether, dibutyl ether, tetrahydrofuran, dioxane, dimethoxyethane, etc.); aromatic solvent (e.g. benzene, toluene, xylene, etc.); protic solvent (e.g. nitromethane, dimethylformamide, dimethylacetamide, dimethylsulfoxide, hexamethylphosphoric triamide, etc.); water; and the like and a mixture thereof can be employed.

When the reaction is carried out preferably in the presence of a base, inorganic bases such as alkali metal hydroxide (e.g. lithium hydroxide, sodium hydroxide, potassium hydroxide, etc.), alkali metal carbonates (e.g. sodium carbonate, potassium carbonate etc.), and alkali metal bicarbonates (e.g. sodium bicarbonate, potassium bicarbonate etc.) or organic bases such as pyridine, dimethylaniline, 4-dimethylaminopyridine, picoline, 2,6-dimethylpyridine, N-methylmorpholine, N-ethylmorpholine, triethylamine, tripropylamine, tributylamine, and the like may be used.

Method B

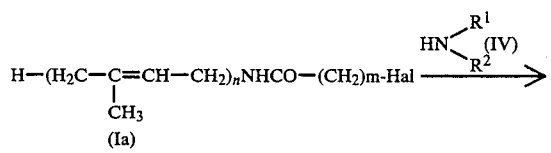

(Ia)

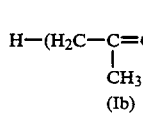

(Ib)

wherein n has the same meaning as defined above; m is an integer of 1 to 5; Hal is halogen (e.g. chlorine, bromine, iodine, etc.); $R^1$ and $R^2$ each is $C_1$-$C_5$ alkyl or taken together may form a saturated heterocyclic group such as pyrrolidinyl, piperidinyl, piperazinyl, morpholinyl, pyrazolidinyl, etc. or an unsaturated heterocyclic group such as pyrrolyl or imidazolyl, and the like; the heterocyclic group may have the substituents such as $C_1$-$C_5$ alkyl.

The compound (Ia) provided in the method A is allowed to react with the amine (IV) in an appropriate solvent at room temperature or under heating (for example, about 50°–about 100° C.) for several ten minutes to several hours to give the objective compound (Ib).

As the solvent, ethers, (e.g. diethyl ether, diisopropyl ether, dibutyl ether, tetrahydrofuran, dioxane, dimethoxyethane, etc.); alkanols (e.g. methanol, ethanol, propanol, isopropanol, butanol, iso-butanol, tert-butanol, etc.); and ketones (acetone, methyl ethyl-ketone, etc.) are employed. As "Hal" of the compound (Ia), iodine is preferable, and in the case of halogen expect for iodine the reaction may be carried out in the presence of alkali an metal iodine (e.g. lithium iodide, sodium iodide, potassium iodide, etc.).

Method C

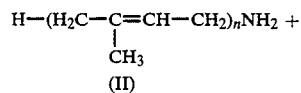

(II)

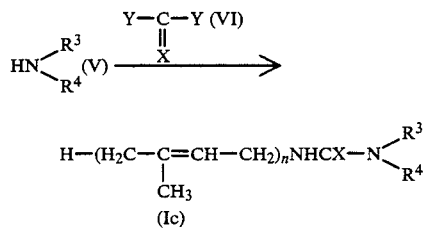

(Ic)

wherein n and X each has the same meaning as defined above; $R^3$ and $R^4$ taken together with the adjacent nitrogen may form the optionally substituted amino; Y is chlorine, bromine, or 1-imidazolyl.

The reaction can be carried out in the same manner as in the usual synthesis of asymmetrical urea derivatives. Thus, one of the prenylamine (II) and the amine (V) are allowed to react with an equimolar amount of a compound (VI) at a temperature under cooling (for example about −50°–about 0° C.), and then the resulting intermediate is allowed to react with an equimolar or excessive amount of the other of the compounds (II) and (V) at a temperature under cooling to a temperature under heating (for example, about −50°–about 100° C.) to give the objective compound (Ic). As the solvent, ethers (e.g. diethyl ether, diisopropyl ether, dibutyl ether, dimethoxyethane, tetrahydrofuran, dioxane etc.); halogenohydrocarbons (e.g. dichloromethane, dichloroethane, chloroform, carbon tetrachloride, etc.); and the like can be employed. The reaction can be accelerated in the presence of a base such as triethylamine, tripropylamine, tributylamine, pyridine, 4-dimethylaminopyridine, dimethylaniline, and the like.

The reaction temperature should be decided according to the properties of the prenylamines (II), the amines (V), and the compounds (VI). The reaction can terminate within a period of about 1 hour to about 50 hours.

Method D

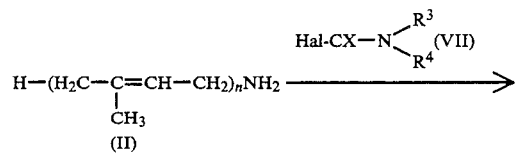

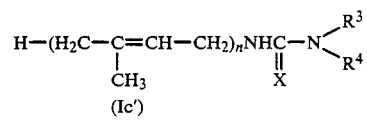

(Ic')

wherein n, X, and Hal each has the same meaning as defined above; $R^3$ and $R^4$ taken together with the adjacent nitrogen atom may form the substituted amino. The reaction may be carried out in the same manner as in the procedure for the customary synthesis of asymmetric urea derivatives.

The objective compound (Ic) may be prepared by reacting the prenylamine (II) with the carbamoyl halide (VII). The reaction can be carried out in an appropriate solvent at a temperature of under cooling (e.g. about −20° to about 0° C.) to room temperature and terminates within a period of several 10 minutes to about 24 hours.

As the solvent water; ethers (e.g. diethyl ether, diisopropyl ether, dibutyl ether, dimethoxyethane, tetrahydrofuran, dioxane, etc.); aromatic solvents (e.g. benzene, toluene, xylene, etc.); halogenohydrocarbons (e.g. dichloromethane, dichloroethane, chloroform, carbon tetrachloride, etc.); dimethylformamide, dimethylsulfoxide; and a mixture thereof can be employed. The reaction may be accelerated by the addition of a base such as triethylamine, tripropylamine, tributylamine, pyridine, dimethylaniline, or the like.

Method E

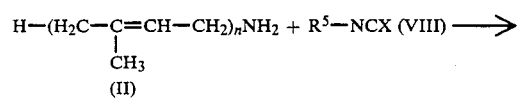

(II)

-continued

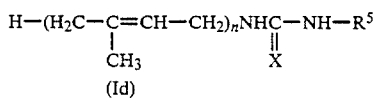
(Id)

wherein n and X each has the same meaning as defined above; $R^5$ is di($C_1$-$C_5$ alkyl)amino-($C_1$-$C_5$ alkyl), phenyl($C_1$-$C_5$ alkyl), halogenophenyl($C_1$-$C_5$ alkyl), 3,4-methylenedioxyphenyl($C_1$-$C_5$ alkyl), morpholinyl-($C_1$-$C_5$ alkyl), pyridyl($C_1$-$C_5$ alkyl), $C_1$-$C_5$ alkyl, phenyl, halogenophenyl, trifluoromethylphenyl, $C_1$-$C_5$ alkoxyphenyl, or 5- or 6- membered heterocyclic group.

The reaction can be carried out in the same manner as in Methods C and D.

The objective compound (Id) may be prepared by the reaction of the prenylamine (II) with the isocyanate or isothiocyanate (VIII) in the same solvent as in Method D. The reaction may be conducted at a temperature of room temperature to a temperature under heating (e.g. about 40° to about 100° C.) and terminates within a period of several hours to about 24 hours.

Method F

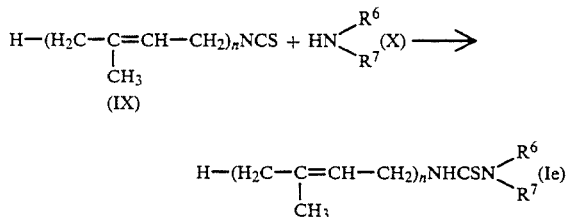

wherein n has the same meaning as defined above; $R^6$ and $R^7$ taken together with the adjacent nitrogen atom may form the optionally substituted amino or saturated heterocyclic group such as pyrrolidinyl, piperidinyl, piperazinyl, morpholinyl, pyrazolidinyl, or the like.

The prenylisothiocyanate (IX) is allowed to react with the compound (X) in a member of the same solvent as used in Method D, preferably in the presence of a base at room temperature to a temperature under heating to give the objective compound (Ie).

The reaction terminates within a period of several hours to several tens of hours.

As the base organic bases such as triethylamine, tripropylamine, tributylamine, pyridine, 4-dimethylaminopyridine, dimethylaniline, and the like or inorganic bases such as sodium hydride, potassium hydride, and the like may be used.

Method G

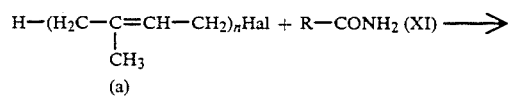

-continued

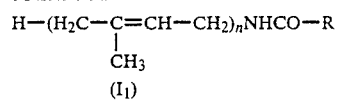
($I_1$)

wherein n and R each has the same meaning as defined above; Hal is halogen.

The objective compound ($I_1$) can be prepared by reacting the halogenoprenyl compound (a) with the acid amide (XI). The reaction may be carried out in an appropriate solvent in the presence of a base. As the solvent tetrahydrofuran, dioxane, dimethylformamide, dimethylsulfoxide, and the like may be used.

As the base alkali metal hydrides such as sodium hydride, potassium hydride, etc. and alkali metal hydroxides such as sodium hydroxide, potassium hydroxide, etc. can be used. When aluminium oxide and potassium hydroxide are used at the same time the compound ($I_1$) can selectively be provided.

The reaction can be accelerated by the addition of phase transfer catalysts such as tetraalkylammonium salts. As the tetraalkylammonium slats, ammonium halides (e.g. chloride, bromide, iodide, etc.), sulfate, or p-toluenesulfonate of 4 members of alkyls selected from the group consisting of methyl, ethyl, propyl, butyl, pentyl, hexyl, heptyl, octyl, nonyl, and decyl can be used. Representatives of the tetraalkylammonium salts are tetramethylammonium bromide, tetaethylammonium bromide, tetrapropylammonium bromide, tetrabutylammonium bromide tetrapentylammonium bromide, tetrahexylammonium bromide, tetraheptylammonium bromide, etc. and the corresponding chloride, iodide, sulfate, p-toluenesulfate, and the like.

The reaction may be carried out at a temperature of about −20° to about 100° C. and terminates within a period of several hours.

Method H

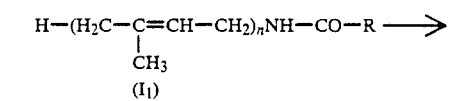

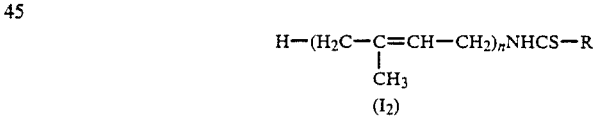

wherein n and R each has the same meaning as defined above.

The compound ($I_2$) can be prepared by reacting the compound ($I_1$) with diphosphorus pentasulfide/pyridine, or Lawesson's Reagent.

As the solvent aromatic solvents such as benzene, toluene, and xylene; halogenohydrocarbons such as dichloromethane, 1,2-dichloroethane, chloroform, and carbon tetrachloride can be used.

The reaction can be carried out at a temperature of room temperature to a temperature under reflux and terminates within a period of several hours.

The starting materials, namely the prenylamines (II) are publicly available or they can be prepared according to the following process (α), (β), and (γ).

Process α

-continued

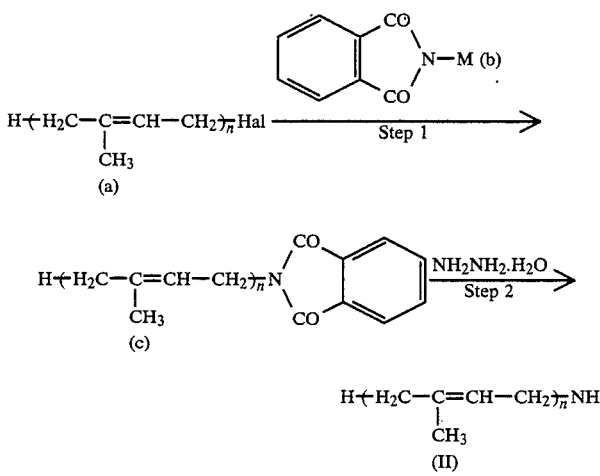

wherein n and Hal each has the same meaning as defined above; M is alkali metal (e.g. lithium, sodium, potassium, etc.)

The reaction can be carried out in accordance with Gabriel's amine synthesis.

In the first step, the N-prenylphthalimide (c) is prepared by reacting the prenyl halide (a) with alkali metal phthalimide (b); and in the second step the prenylamine (II) is provided by reacting the compound (c) with hydrazine hydrate in an appropriate solvent.

The reaction in the first step may be carried out at a temperature of about 50° to about 100° C. and terminates within a period of several ten minutes to several hours.

As the solvent, aprotic solvents (e.g. nitromethane, dimethylformamide, dimethylacetamide, dimethylsulfoxide, hexamethylphosphoric triamide, etc.); ethers (e.g. tetrahydrofuran, dioxane, dimethoxyethane, etc.); aromatic solvents (e.g. benzene, toluene, xylene, etc.) and the like can be employed.

The reaction in the second step is preferably carried out under heating (for example, about 50° to about 100° C.), and it terminates within a period of several ten minutes to several hours. Alkanols such as methanol, ethanol, propanol, isopropanol, butanol, isobutanol, tert-butanol, etc. can be used.

Process β

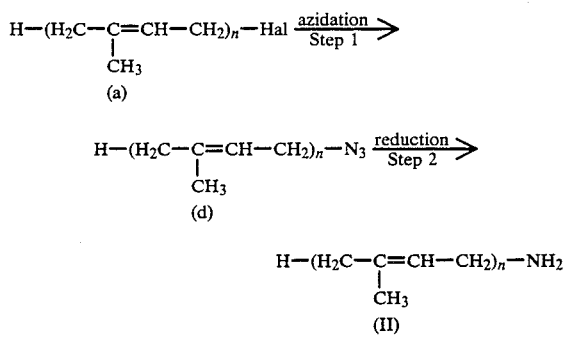

wherein n and Hal each has the same meaning as defined above

The reaction conditions in Steps 1 and 2 will be explained below.

Step 1

In this step the prenyl halide is subjected to azidation. As the reagent for azidation, alkali metal azide (e.g. lithium azide, sodium azide, potassium azide, etc.) or trimethylsilyl azide and the like can be used. The reaction is carried out in an appropriate solvent, and when alkali metal azide is used, the reaction is preferably conducted in the presence of a phase transfer catalyst.

As the solvent, ethers (e.g. diethyl ether, diisopropyl ether, dimethoxyethane, tetrahydrofuran, dioxane, etc.); haogenohydrocarbons (e.g. dichloromethane, dichloroethane, chloroform, carbon tetrachloride, etc.); aliphatic hydrocarbons (e.g. cyclohexane, etc.); aprotic solvents (e.g. nitromethane, dimethylformamide, dimethylacetamide, dimethylsulfoxide, hexamethylphosphoric triamide); and the like may be employed.

As the phase transfer catalyst, tetraalkylammonium salt (e.g. tetrabutylammonium bromide, etc.) may be utilized.

The reaction is carried out from room temperature to about 50° ~ about 100° C. and terminates within a period of about 30 minutes to several hours.

Step 2

The prenylamine (II) is prepared by reducing the prenylazide (d).

The reduction can be conducted by using metal hydrides [e.g. lithium aluminum hydride, diisobutyl aluminum hydride, sodium borohydride, etc.]; metal and acid [e.g. zinc-acetic acid, etc.]; and methal amalgam [e.g. sodium-mercury].

The reaction may be carried out in an appropriate solvent at a temperature of about −50° to about 100° C. and terminates within a period of about 1 to several hours.

The solvent should be selected from the group consisting of ethers (e.g. diethyl ether, diisopropyl ether, tetrahydrofuran, dioxane, dimethoxyethane, etc.); aliphatic hydrocarbons (e.g. pentane, hexane, cyclohexane, etc.); aromatic solvents (e.g. benzene, toluene, xylene, etc.); alkanols (e.g. methanol, ethanol, propanol, isopropanol, butanol, isobutanol, tert-butanol, etc.); and the like.

Process γ

-continued

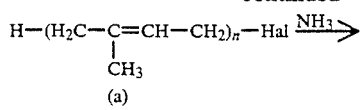
(a)

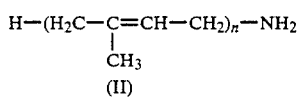
(II)

wherein n and Hal each has the same meaning as defined above.

The prenylamine (II) can be prepared by reacting a solution of prenyl halide (a) in ammonia et a temperature of under cooling to room temperature for several hours to about 48 hours.

The reaction is preferably conducted in the presence of alkali metal amide (e.g. sodium amide, potassium amide, etc.) in a sealed tube.

The prenyl halide (a) used in Method G, Process α, Process β, and Process γ can be provided by the halogenation of the alkohol (e) or (f).

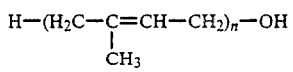

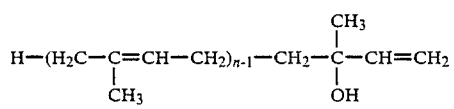

The isothiocyanate (IX) can be provided from the prenylamine (II) according to the following Process δ.

Process δ

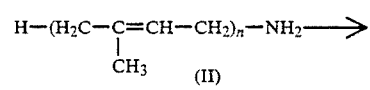
(II)

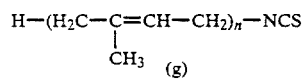
(g)

wherein n has the same meaning as defined above.

The prenylamine (II) is subjected to the usual isothiocyanate formation reaction. For example, the prenylamine (II) is allowed to first react with carbon disulfide in the presence of an appropriate base, and secondly with an ester of chlorocarbonate (e.g. methyl ester, ethyl ester, etc.)

The base includes triethylamine, morpholine, piperidine, pyrrolidine, and the like.

In place of the ester of chlorocarbonate, 1-methyl-2-chloropyridinium salt may be used.

The compound (I) of the present invention can exist as stereoisomers relative to the E and Z configuration. Each stereoisomer of (I) can be prepared from the corresponding stereo-isomeric alcohol (e) through prenylamine (II).

[E,E,E]-Tetraprenol:3,7,11,15-tetramethyl-2,6,10,14-hexadecatetraenol is publicly aware; [Z,E,E]-tetraprenol, [E,E,Z]-tetraprenol, and [Z,E,Z]-tetraprenol as well as [E,E,E]-tetraprenol can be prepared according to the methods described in Naruta et al., Journal of Organic Chemistry 45 (21), 4097 (1980) and Y. Masaki et al., Tetrahedron 4 (18), 3481 (1984). [Z,Z,Z]--Tetraprenol is also publicly aware; and [Z,Z,E]-tetraprenol, [E,Z,Z]-tetraprenol, and [E,Z,E]-tetraprenol can be prepared in the same manner as described in S. Kikumasa et al, Tetrahedron Letter or they can be prepared in the manner as in Referential Example.

The compounds (I) of the present invention may form a complex with a cyclodextrin. As the cyclodextrin, β-cyclodextrin and γ-cyclodextrin are preferred.

The novel complex is useful for stabilization of the host compound (I) and the preparation. For example, the complex containing the compound (I) is solid, therefore it can easily be prepared in the form of powder, fine granule, or granule. Thus, the complex is useful as an antiulcer agent.

The complex can be prepared in the usual manner. A mixture of a solution of the compound in alkanol or in water and an aqueous cyclodextrin is stirred room temperature for about 20-50 hours to give the precipitate of the complex. More than 1 mole equivalent of cyclodextrin preferably 2 to 5 moles equivalents of cyclodextrin for the compound (I) may be used.

The compound (I) of the present invention can be converted into pharmaceutically acceptable acid addition salts thereof, and the acid addition salts are also effective and included in this invention. The acid which can form the salt is exemplified by inorganic acids such as hydrohaogenic acid (e.g. hydrochloric acid, hydrobromic acid, etc.); sulfuric acid, nitric acid, phosphoric acid, and the like; and organic acids such as acetic acid, propionic acid, oxalic acid, malonic acid, succinic acid, glutaric acid, adipic acid, malic acid, maleic acid, fumaric acid, citric acid, benzoic acid, methanesulfonic acid, and the like.

The compound (I) can be administered orally or parenterally to humans or animals.

The compound (I) or the complex with cyclodextrin can be administered orally in the form of tablets, granule, powder, capsules, or liquid, and parenterally in the form of injection. These preparations can be prepared in a conventional manner by addition of diluents, binders, disintegrators, lubricants, stabilizers, corrigents, suspending agents, dispersants, solubilizers, antiseptics, and the like. As the diluents, lactose, sucrose, starch, cellulose, sorbit, etc.; as the binders, gumarabic, geratin, polyvinylpyrrolidone, etc.; as the lubricants, magnesium stearate, talc, silica-gel, etc. can be employed.

When the compounds (I) are used in treatment of peptic ulcer of adults, about 1~500 mg-kg of the compound (I) is administered orally or parenterally per day.

The present invention will be explained in more detail by the following Examples, Referential Examples, and Preparation.

The abbreviations used in Examples, Referential Examples, and Tables each has the following meaning.

MeOH: methanol; EtOH: ethanol; $CH_2Cl_2$: dichloromethane; NaH: sodium hydride (60% oil dispersion); KOH: potassium hydroxide; NaOH: sodium hydroxide; $NaHCO_3$: sodium bicarbonate; $Et_3N$: triethylamine; AcOEt: ethyl acetate; $Et_2O$: diethyl ether; i-Bu: isobutyl.

EXAMPLE 1

N-(3,7,11,15-Tetramethyl-2,6,10,14-hexadecatetraenyl)-formamide I-1

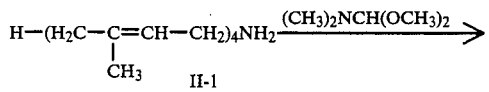

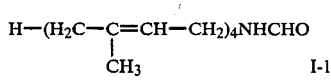

To a stirred solution of 580 mg (2 mmol) of 3,7,11,15-tetramethyl-2,6,10,14-hexadecatetraenylamine (hereinafter abbreviated as tetraprenylamine) II-1 in 20 ml of anhydrous tetrahydrofuran is added 953 mg (8 mmol) of N,N-dimethylformamide dimethylacetal. The mixture is heated under reflux for 3 hours, mixed with 15 ml of 10% aqueous sodium carbonate, and stirred at room temperature for 4 hours. The reaction mixture is concentrated, and the resulting residue is dissolved in 50 ml of $CH_2Cl_2$ and washed twice with 50 ml of water. The resulting mixture is dried over anhydrous sodium sulfate and evaporated under reduced pressure. The residue is purified by silica-gel column chromatography and eluted with AcOEt to give 410 mg of the titled compound I-1 as colorless oil.

Yield: 64.7%.

EXAMPLE 2

N-(3,7,11,15-Tetramethyl-2,6,10,14-hexadecatetraenyl)acetamide I-2

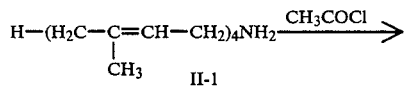

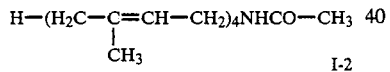

To a solution (10 ml) of 10% sodium hydroxide is added 580 mg (2 mmol) of tetraprenylamine II-1 in 20 ml of $CH_2Cl_2$. The mixture is mixed with 0.5 ml of acetyl chloride under ice-cooling and stirred vigorously at room temperature for 2 hours. After the termination of the reaction, $CH_2Cl_2$ layer is collected and washed with 20 ml of saturated aqueous $NaHCO_3$, and twice with 20 ml of water. The resulting mixture is dried over anhydrous sodium sulfate and evaporated under reduced pressure. The residual oil is purified by silica-gel column chromatography and eluted with AcOEt to give 712 mg of the titled compound I-2 as colorless oil.

Yield: 83.3%.

EXAMPLES 3–6

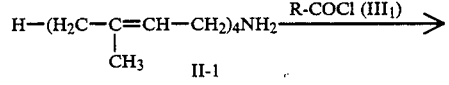

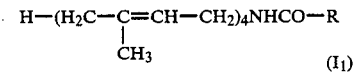

wherein R has the same meaning as defined above.

To a stirred mixture of 580 mg (2 mmol) of tetraprenylamine II-1, 20 ml of $CH_2Cl_2$, and 10 ml of 10% aqueous NaOH is added a solution of 2.5 mmol of the compound ($III_1$) in 5 ml of $CH_2Cl_2$. The mixture is stirred at room temperature for 2 hours. After the termination of the reaction, $CH_2Cl_2$ layer is collected and washed with 20 ml of saturated aqueous $NaHCO_3$ and twice with 20 ml of water. The resulting mixture is dried over anhydrous sodium sulfate and evaporated under reduced pressure. The residual oil is purified by silica-gel column chromatography and eluted with an appropriate eluent to give the objective compound ($I_1$).

Compound number, structural formula, yield of the each objective compound ($I_1$) provided in Examples 3-6 and eluent used for silica-gel column chromatography will be shown in Table 1.

TABLE 1

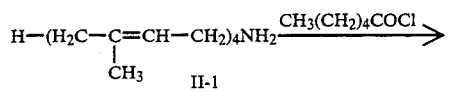

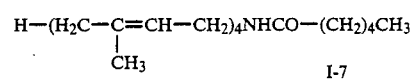

| Ex. No. | Compd. No. | R of the compound ($I_1$) and the compound ($III_1$) | Eluent (v/v) | Yield (%) |
|---|---|---|---|---|
| 3 | I-3 | $CH_2Cl$ | $Et_2O$:hexane (2:1) | 92.9 |
| 4 | I-4 | $CH_2OCH_3$ | $Et_2O$ | 95.2 |
| 5 | I-5 | $CH_2CH_2Cl$ | $Et_2O$:hexane (1:1) | 92.5 |
| 6 | I-6 | $CH_2CH_2CH_2Cl$ | $Et_2O$:hexane (1:1) | 91.5 |

EXAMPLE 7

N-(3,7,11,15-Tetramethyl-2,6,10,14-hexadecatetraenyl)-n-hexanoylamide I-7

To a stirred solution of 580 mg (2 mmol) of tetraprenylamine II-1 and 222 mg (2.2 mmol) of $Et_3N$ in 20 ml of $CH_2Cl_2$ is added 5 ml of a solution of 296 mg (2.2 mmol) of n-hexanoyl chloride in $CH_2Cl_2$ with ice-water cooling. The mixture is allowed to stand at room temperature for 24 hours. The reaction mixture is washed twice with 20 ml of saturated $NaHCO_3$ and twice with 20 ml of water, dried over anhydrous sodium sulfate, and evaporated under reduced pressure. The resulting residual oil is purified by silica-gel column chromatography and eluted with $Et_2O$:hexane (1:1 v/v) to give 611 mg of the titled compound I-7 as colorless oil.

Yield: 78.8%.

EXAMPLES 8–15

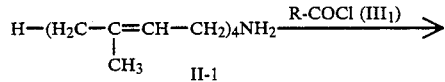

-continued $$H-(H_2C-\underset{\underset{CH_3}{|}}{C}=CH-CH_2)_4NHCO-R \quad (I_1)$$

wherein R has the same meaning as defined above.

To a stirred solution of of tetraprenylamine II-1 and 222 mg (2.2 mmol) of Et₃N in 20 ml of CH₂Cl₂ is added a solution of 2.2 mmol of the compound (III₁) in 5 ml of CH₂Cl₂. The mixture is stirred at room temperature for 24 hours. The reaction mixture is washed twice with 20 ml of saturated aqueous NaHCO₃ and twice with 20 ml of water. The resulting mixture is dried over anhydrous sodium sulfate and evaporated under reduced pressure. The residual oil is purified by silica-gel column chromatography and eluted with an appropriate eluent to give the objective compound (I₁).

Compound number, structural formula, yield of the each objective compound (I₁) provided in Examples 8–15 and eluent used for silica-gel column chromatography will be shown in Table 2.

TABLE 2

$$H-(H_2C-\underset{\underset{CH_3}{|}}{C}=CH-CH_2)_4NH_2 + R-COCl \xrightarrow{Et_3N}$$
$$\text{II-1} \qquad (III_1)$$

$$H-(H_2C-\underset{\underset{CH_3}{|}}{C}=CH-CH_2)_4NH-CO-R$$
$$(I_1)$$

| Ex. No. | Compd. No. | R of the compound (I₁) and the compound (III₁) | Eluent (v/v) | Yield (%) |
|---|---|---|---|---|
| 8 | I-8 | —(CH₂)₁₄—CH₃ | Et₂O:hexane (1:3) | 95.5 |
| 9 | I-9 |  | Et₂O:hexane (1:1) | 93.2 |
| 10 | I-10 | —Cl | Et₂O:hexane (1:2) | 82.7 |
| 11 | I-11 | 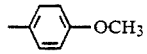—OCH₃ | Et₂O:hexane (1:1) | 96.4 |
| 12 | I-12 |  | Et₂O:hexane (1:1) | 94.6 |
| 13 | I-13 | —CH₂—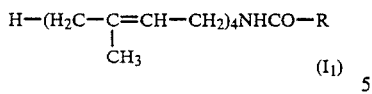 | Et₂O:hexane (1:1) | 92.2 |
| 14 | I-14 | —CH₂—O—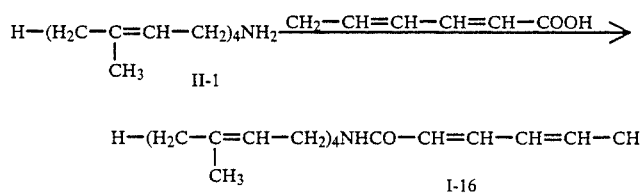 | Et₂O:hexane (1:1) | 91.8 |

TABLE 2-continued $$H-(H_2C-\underset{\underset{CH_3}{|}}{C}=CH-CH_2)_4NH_2 + R-COCl \xrightarrow{Et_3N}$$
$$\text{II-1} \qquad (III_1)$$

$$H-(H_2C-\underset{\underset{CH_3}{|}}{C}=CH-CH_2)_4NH-CO-R$$
$$(I_1)$$

| Ex. No. | Compd. No. | R of the compound (I₁) and the compound (III₁) | Eluent (v/v) | Yield (%) |
|---|---|---|---|---|
| 15 | I-15 | —CH(CH₃)—O—⟨ ⟩ | Et₂O:hexane (1:1) | 92.9 |

EXAMPLE 16

N-(3,7,11,15-Tetramethyl-2,6,10,14-hexadecatetraenyl)-2,4-hexadienoylamide I-16

$$H-(H_2C-\underset{\underset{CH_3}{|}}{C}=CH-CH_2)_4NH_2 \xrightarrow{CH_3-CH=CH-CH=CH-COOH}$$
$$\text{II-1}$$

$$H-(H_2C-\underset{\underset{CH_3}{|}}{C}=CH-CH_2)_4NHCO-CH=CH-CH=CH-CH_3$$
$$\text{I-16}$$

A mixture of 580 mg (2 mmol) of tetraprenylamine II-1, 247 mg (2.2 mmol) of sorbic acid, 562 mg (2.2 mmol) of 2-chloro-1-methylpyridinium iodide, and 444 mg (4.4 mmol) of Et₃N in 20 ml of CH₂Cl₂ is heated under reflux for 3 hours. After the termination of the reaction, the reaction mixture is washed twice with 20 ml of saturated aqueous NaHCO₃ and twice with 20 ml of water. The mixture is dried over anhydrous sodium sulfate and evaporated under reduced pressure. The resulting residual oil is purified by silica-gel column chromatography and eluted with Et₂O:hexane (1:1 v/v) to give 651 mg of the titled compound I-16 as yellowish oil.

Yield: 84.8%.

EXAMPLES 17–44

$$H-(H_2C-\underset{\underset{CH_3}{|}}{C}=CH-CH_2)_4NH_2 \xrightarrow{R-COOH \, (III_2)}$$
$$\text{II-1}$$

$$H-(H_2C-\underset{\underset{CH_3}{|}}{C}=CH-CH_2)_4NHCO-R$$
$$(I_1)$$

wherein R has the same meaning as defined above.

A mixture of 580 mg of tetraprenylamine II-1, 2.2 mmol of a carboxylic acid (III₂) or the hydrochloride, 562 mg (2.2 mmol) of 2-chloro-1-methylpyridinium iodide, 444 mg (4.4 mmol) of Et₃N [when hydrochloride of the compound (III₂) is used 666 mg (6.6 mmol) of Et₃N is employed] in 20 ml of CH₂Cl₂ is heated under reflux for 3 hours. After the termination of the reaction, the reaction mixture is washed twice with 20 ml of saturated aqueous NaHCO₃ and twice with 20 ml of water. The mixture is dried over anhydrous sodium sulfate and evaporated under reduced pressure. The resulting oil is purified by silica-gel column chromatography and eluted with an appropriate eluent to give the objective compound (I₁).

Compound number, structural formula, and yield of the each objective compound (I₁) provided in Examples 17–44 and eluent used for silica-gel column chromatography will be shown in Table 3.

TABLE 3

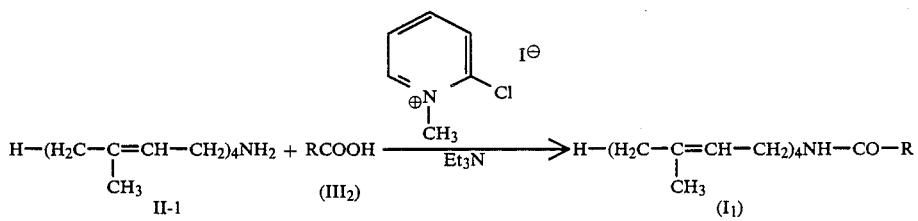

H—(H₂C—C(CH₃)=CH—CH₂)₄NH₂ + RCOOH  →[Et₃N]  H—(H₂C—C(CH₃)=CH—CH₂)₄NH—CO—R
      (II-1)                  (III₂)                                    (I₁)

| Ex. No. | Compd. No. | R of the compound (I₁) and the compound (III₂) | Eluent (v/v) | Yield (%) |
|---|---|---|---|---|
| 17 | I-17 | —(CH₂)₂—CH=C(CH₃)—(CH₂)₂—CH=C(CH₃)—CH₃ | Et₂O:hexane (1:1) | 53.8 |
| 18 | I-18 | —C₆H₄—NO₂ (p-nitrophenyl) | Et₂O:hexane (1:2) | 65.0 |
| 19 | I-19 | —C₆H₄—N(CH₃)₂ (p-dimethylaminophenyl) | Et₂O:hexane (2:1) | 79.2 |
| 20 | I-20 | 2-pyridyl | Et₂O | 62.6 |
| 21 | I-21 | 3-pyridyl | AcEt | 56.8 |
| 22 | I-22 | 4-pyridyl | AcEt | 62.4 |
| 23 | I-23 | 2-furyl | Et₂O:hexane (1:1) | 59.2 |
| 24 | I-24 | 2-thienyl | Et₂O:hexane (1:1) | 72.5 |
| 25 | I-25 | 3-thienyl | Et₂O:hexane (1:1) | 65.6 |
| 26 | I-26 | 2-pyrrolyl | Et₂O:hexane (1:1) | 70.0 |
| 27 | I-27 | 2-indolyl | Et₂O | 59.3 |

TABLE 3-continued $$\text{H—(H}_2\text{C—C=CH—CH}_2)_4\text{NH}_2 + \text{RCOOH} \xrightarrow[\text{Et}_3\text{N}]{\text{2-chloro-1-methylpyridinium iodide}} \text{H—(H}_2\text{C—C=CH—CH}_2)_4\text{NH—CO—R}$$
$$\text{CH}_3 \qquad\qquad\qquad\qquad\qquad\qquad\qquad \text{CH}_3$$
$$\text{(II-1)} \quad \text{(III}_2\text{)} \qquad\qquad\qquad\qquad\qquad \text{(I}_1\text{)}$$

| Ex. No. | Compd. No. | R of the compound (I₁) and the compound (III₂) | Eluent (v/v) | Yield (%) |
|---|---|---|---|---|
| 28 | I-28 | pyrazinyl (methylpyrazine) | Et₂O:AcOEt (1:1) | 66.2 |
| 29 | I-29 | —CH₂-(2-pyridyl) | AcEt | 43.7 |
| 30 | I-30 | —CH₂-(3-pyridyl) | AcOEt | 76.4 |
| 31 | I-31 | —CH₂-(imidazolyl) | MeOH:AcOEt (1:5) | 27.7 |
| 32 | I-32 | —CH(phenyl)₂ | Et₂O:hexane (1:2) | 89.4 |
| 33 | I-33 | —CH=CH—phenyl | Et₂O:hexane (1:1) | 75.8 |
| 34 | I-34 | —CH=CH—(3-pyridyl) | AcOEt | 68.0 |
| 35 | I-35 | —CH=CH—(imidazolyl) | MeOH:AcOEt (1:5) | 38.9 |
| 36 | I-36 | —CH₂CN | Et₂O | 63.4 |
| 37 | I-37 | —CH₂NHCO—phenyl | Et₂O:AcOEt (1:1) | 41.6 |

TABLE 3-continued $$\text{H—(H}_2\text{C—C=CH—CH}_2)_4\text{NH}_2 + \text{RCOOH} \xrightarrow[\text{Et}_3\text{N}]{\text{[2-chloro-1-methylpyridinium iodide]}} \text{H—(H}_2\text{C—C=CH—CH}_2)_4\text{NH—CO—R}$$
$$\quad\quad\quad\quad \text{CH}_3 \quad\quad\quad\quad\quad\quad\quad\quad\quad\quad\quad\quad\quad\quad\quad\quad\quad\quad\quad\quad \text{CH}_3$$
$$\quad\quad\quad\quad\quad \text{II-1} \quad\quad\quad (\text{III}_2) \quad\quad\quad\quad\quad\quad\quad\quad\quad\quad\quad\quad\quad\quad\quad\quad (\text{I}_1)$$

| Ex. No. | Compd. No. | R of the compound (I₁) and the compound (III₂) | Eluent (v/v) | Yield (%) |
|---|---|---|---|---|
| 38 | I-38 | 5-butyl-2-pyridyl group | Et₂O:hexane (1:2) | 70.2 |
| 39 | I-39 | 3-methyl-2-[(3-trifluoromethylphenyl)amino]pyridyl group | Et₂O:hexane (1:2) | 83.1 |
| 40 | I-40 | [1-(4-chlorobenzoyl)-5-methoxy-2-methylindol-3-yl]methyl group | Et₂O | 75.2 |
| 41 | I-41 | 3,5-di-tert-butyl-4-hydroxyphenyl group | Et₂O:hexane (1:1) | 47.9 |
| 42 | I-42 | —CH₂—(4-pyridyl) | MeOH:AcOEt (1:10) | 66.5 |
| 43 | I-43 | —CH₂CH₂—(2-pyridyl) | MeOH:AcOEt (1:20) | 75.3 |
| 44 | I-44 | —CH₂CH₂—(4-pyridyl) | MeOH:AcOEt (1:15) | 80.1 |

EXAMPLE 45

N-(3,7,11,15-Tetramethyl-2,6,10,14-hexadecatetraenyl)-2-(4-isobutylphenyl)propionamide I-45

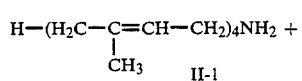 +

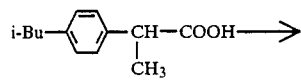

-continued

23
-continued

H—(H₂C—C(CH₃)=CH—CH₂)₄NHCO—CH(CH₃)—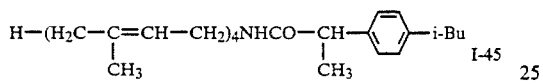—i-Bu   I-45

To a solution of 454 mg (2.2 mmol) of ibuprofen in 20 ml of CH₂Cl₂ are added 310 μl of Et₃N and 310 μl of ethyl chlorocarbonate with ice-cooling under stirring. The mixture is stirred for 15 minutes at the same temperature and for further 15 minutes at room temperature. The reaction mixture is mixed with 580 mg (2 mmol) of tetraprenylamine II-1 and stirred at room temperature for 2 hours. The reaction mixture is washed twice with 20 ml of saturated aqueous NaHCO₃ and with 20 ml of water. The mixture is dried over anhydrous sodium sulfate and evaporated under reduced pressure. The resulting oil is purified by silica-gel column chromatography and eluted with Et₂O:hexane (1:1 v/v) to give 837 mg of the titled compound I-45. Yield: 84.4 %.

EXAMPLES 46–47

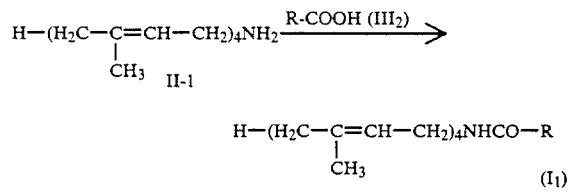

To a solution of 454 mg (2.2 mmol) of the compound (III₂) in 20 ml of CH₂Cl₂ are added 310 μl of Et₃N and 310 μl of ethyl chlorocarbonate with ice-cooling under stirring. The mixture is stirred for 15 minutes at the same temperature and for further 15 minutes at room temperature. The reaction mixture is mixed with 580 mg (2 mmol) of tetraprenylamine II-1 and stirred at room temperature for 2 hours. The reaction mixture is washed twice with 20 ml of saturated aqueous NaHCO₃ and with 20 ml of water. The mixture is dried over anhydrous sodium sulfate and evaporated under reduced pressure. The resulting oil is purified by silicagel column chromatography and eluted with an appropriate eluent to give the objective compound (I₁).

Compound number, structural formula, yield of the each objective compound (I₁) provided in Examples 46,

24 and 47 and eluent used for silica-gel column chromatography will be shown in Table 4.

TABLE 4

H—(H₂C—C(CH₃)=CH—CH₂)₄NH₂ + R—COOH $\xrightarrow[\text{Et}_3\text{N}]{\text{ClCOOEt}}$

II-1      (III₂)

H—(H₂C—C(CH₃)=CH—CH₂)₄NH—CO—R    (I₁)

| Ex. No. | Compd. No. | R of the compound (I₁) and the compound (III₂) | Eluent (v/v) | Yield (%) |
|---|---|---|---|---|
| 46 | I-46 | 2-methylphenyl-OCOCH₃ (o-acetoxytolyl) | Et₂O:hexane (1:1) | 86.1 |
| 47 | I-47 | —CH₂CH₂—(4-pyridyl) | MeOH: AcOEt (1:20) | 64.7 |

EXAMPLE 48

2-(N,N-Diethylamino)-N'-(3,7,11,15-tetramethyl-2,6,10,14-hexadecatetraenyl)acetamide I-48

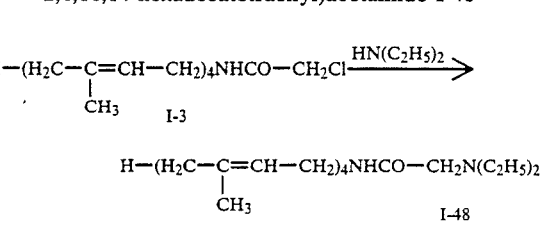

A mixture of 1.46 g (4 mmol) of N-(3,7,11,15-tetramethyl-2,6, 10,14-hexadecatetraenyl)chloroacetamide I-3 provided in Example 3, 731 mg (10 mmol) of diethylamine, 749 mg (5 mmol) of sodium iodide in 40 ml of acetone is heated under reflux for 3 hours and allowed to stand at room temperature overnight. The reaction mixture is filtered and evaporated under reduced pressure. The residue is dissolved in 100 ml of Et₂O, washed 3 times with 100 ml of water, dried over anhydrous sodium sulfate, and evaporated under reduced pressure. The resulting oil is purified by silica-gel column chromatography and eluted with MeOH:AcOEt (1:10 v/v) to give 1.48 g of the titled compound I-48.

Yield: 91.9%.

EXAMPLES 49–53

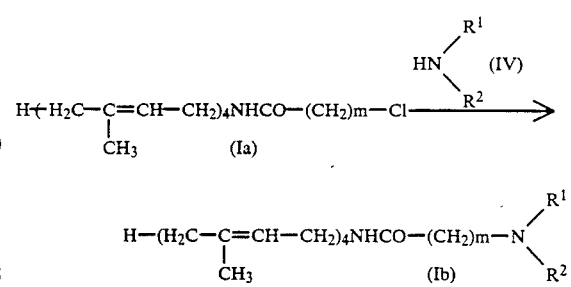

wherein m, R¹, and R² each has the same meaning as defined above.

A mixture of 2 mmol of the compound (Ia), 5 mmol of the amine (IV), 2.5 mmol of sodium iodide in 20 ml of acetone is heated under reflux for 3 hours and allowed to stand at room temperature overnight. The reaction mixture is filtered and evaporated under reduced pressure. The residue is dissolved in 100 ml of Et$_2$O, washed 3 times with 100 ml of water, dried over anhydrous sodium sulfate, and evaporated under reduced pressure. The resulting oil is purified by silica-gel column chromatography and eluted with an appropriate eluent to give the objective compound (Ib).

Compound number, structural formula, and yield of the each objective compound (Ib) provided in Examples 49–53 and eluent used for silica-gel column chromatography will be shown in Table 5.

TABLE 5

H—(H$_2$C—C(CH$_3$)=CH—CH$_2$)$_4$NH—CO—(CH$_2$)m-Cl + HNR$^1$R$^2$ (IV) $\xrightarrow{\text{NaI}}$ H—(H$_2$C—C(CH$_3$)=CH—CH$_2$)$_4$NH—CO—(CH$_2$)m—NR$^1$R$^2$ (Ib)

| Ex. No. | Compd. No. | m | —NR$^1$R$^2$ | Eluent (v/v) | Yield (%) |
|---|---|---|---|---|---|
| 49 | I-49 | 1 | —N(morpholino) | AcOEt | 95.6 |
| 50 | I-50 | 1 | —N(piperazinyl-pyridyl) | Et$_2$O:AcOEt (1:1) | 94.5 |
| 51 | I-51 | 1 | —N(imidazolyl) | MeOH:AcOEt (1:5) | 53.8 |
| 52 | I-52 | 2 | —N(n-C$_3$H$_7$)$_2$ | MeOH:AcOET (1:2) | 25.0 |
| 53 | I-53 | 3 | —N(C$_2$H$_5$)$_2$ | MeOH | 20.0 |

EXAMPLE 54

1-[N-(3,7,11,15-Tetramethyl-2,6,10,14-hexadecatetraenyl)-carbamoyl]imidazole I-54

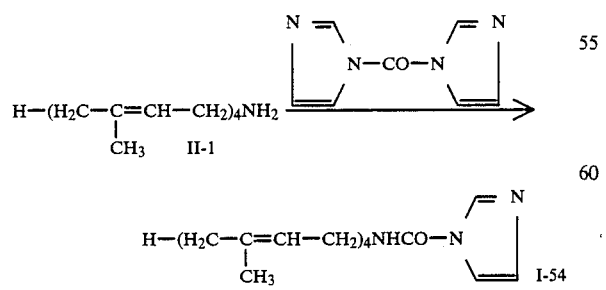

To a solution of 746 mg (2.5 mmol) of tetraprenylamine II-1 in 30 ml of CH$_2$Cl$_2$ is added 486 mg (3 mmol) of N,N'-carbonyldiimidazole. The mixture is stirred at −20~0° C. for 2 hours. The reaction mixture is evaporated and the resulting residue is purified by silica-gel column chromatography and eluted with AcOEt to give 620 mg of the titled compound I-54 as colorless oil. Yield: 64.7%.

EXAMPLE 55

1-[N-(3,7,11,15-Tetramethyl-2,6,10,14-hexadecatetraenyl)carbamoyl]morpholine I-55

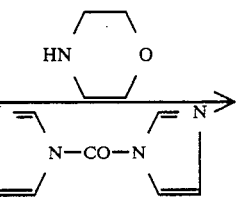

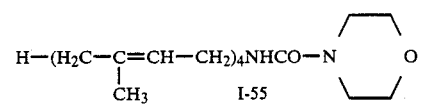

To a solution of 580 mg (2 mmol) of tetraprenylamine II-1 in 20 ml of CH$_2$Cl$_2$ is added 357 mg (2.2 mmol) of N,N'-carbonyldiimidazole. The mixture is stirred at −20°~0° C. for 30 minutes and at 0° C. to room temperature for 1 hour. The reaction mixture is mixed with 218 mg (2.5 mmol) of morpholine and allowed to stand at room temperature for 24 hours. The resulting mixture is washed twice with 20 ml of water, dried over anhydrous sodium sulfate, and evaporated under reduced pressure. The resulting oil is purified by silica-gel column chromatography and eluted with AcOEt to give 769 mg of the titled compound I-55 as colorless oil. Yield: 94.6%.

EXAMPLES 56–75

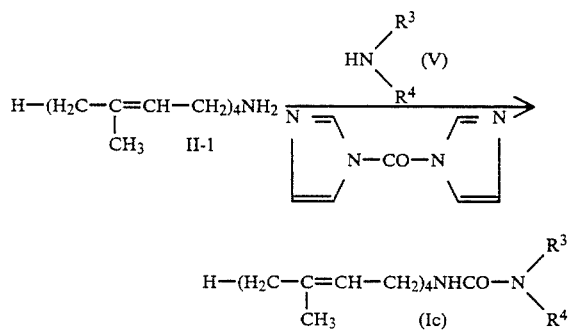

wherein $R^3$ and $R^4$ each has the same meaning as defined above.

To a solution of 580 mg (2 mmol) of tetraprenylamine II-1 in 20 ml of $CH_2Cl_2$ is added 357 mg (2.2 mmol) of N,N'-carbonyldiimidazole at $-20°$ C. The mixture is stirred at $-20° \sim 0°$ C. for 30 minutes and at a temperature of 0° C. to room temperature for 1 hour. The mixture is mixed with 2.5 mmol of the compound (V) and allowed to stand at room temperature for 24 hours. The reaction mixture is washed twice with 20 ml of water, dried over anhydrous sodium sulfate, and evaporated under reduced pressure. The resulting oil is purified by silica-gel column chromatography and eluted with an appropriate eluent to give the objective compound (Ic).

Compound number, structural formula, and yield of the each objective compound (Ic) provided in Examples 56–75 and eluent used for silica-gel column chromatography will be shown in Table 6.

TABLE 6

| Ex. No. | Compd. No. | $-N\begin{smallmatrix}R^3\\R^4\end{smallmatrix}$ | Eluent (v/v) | Yield (%) |
|---|---|---|---|---|
| 56 | I-56 | —N(piperidinyl) | Et₂O:hexane (2:1) | 86.0 |
| 57 | I-57 | —NH₂ | AcOEt | 54.9 |
| 58 | I-58 | —N(piperazinyl)N—CO₂C₂H₅ | Et₂O:AcOEt (5:1) | 61.7 |
| 59 | I-59 | —N(piperazinyl)NCH₃ | MeOH | 88.7 |
| 60 | I-60 | —N(piperazinyl)N—C₆H₅ | Et₂O | 92.5 |
| 61 | I-61 | —N(piperazinyl)N—(2-pyridyl) | Et₂O | 73.2 |

TABLE 6-continued $$H-(H_2C-\underset{CH_3}{\underset{|}{C}}=CH-CH_2)_4NH_2 + HN\underset{R^4}{\overset{R^3}{\diagup}} \quad \xrightarrow{\text{(reagent)}}$$

II-1 (V)

$$H-(H_2C-\underset{CH_3}{\underset{|}{C}}=CH-CH_2)_4NH-CO-N\underset{R^4}{\overset{R^3}{\diagup}} \quad (Ic)$$

| Ex. No. | Compd. No. | $-N\overset{R^3}{\underset{R^4}{\diagup}}$ | Eluent (v/v) | Yield (%) |
|---|---|---|---|---|
| 62 | I-62 | 4-(3,4-methylenedioxybenzyl)piperazin-1-yl | AcOEt | 87.0 |
| 63 | I-63 | —NHCH$_2$CH$_2$N(CH$_3$)$_2$ | NH$_4$OH:MeOH (1:100) | 90.4 |
| 64 | I-64 | —NHCH$_2$CH$_2$N(morpholino) | MeOH:AcOEt (1:2) | 99.2 |
| 65 | I-65 | —NH(CH$_2$)$_3$—N(morpholino) | MeOH:AcOEt (1:2) | 92.5 |
| 66 | I-66 | —NHCH$_2$C$_6$H$_5$ | Et$_2$O | 47.4 |
| 67 | I-67 | —NHCH$_2$-(4-Cl-C$_6$H$_4$) | Et$_2$O:hexane (10:1) | 50.1 |
| 68 | I-68 | —NHCH$_2$-(3,4-methylenedioxyphenyl) | Et$_2$O | 49.3 |
| 69 | I-69 | —NHCH$_2$CH$_2$C$_6$H$_5$ | Et$_2$O | 80.5 |
| 70 | I-70 | —NHCH$_2$-(2-pyridyl) | MeOH:AcOEt (1:10) | 57.0 |
| 71 | I-71 | —NHCH$_2$-(3-pyridyl) | MeOH:AcOEt (1:10) | 60.3 |

TABLE 6-continued

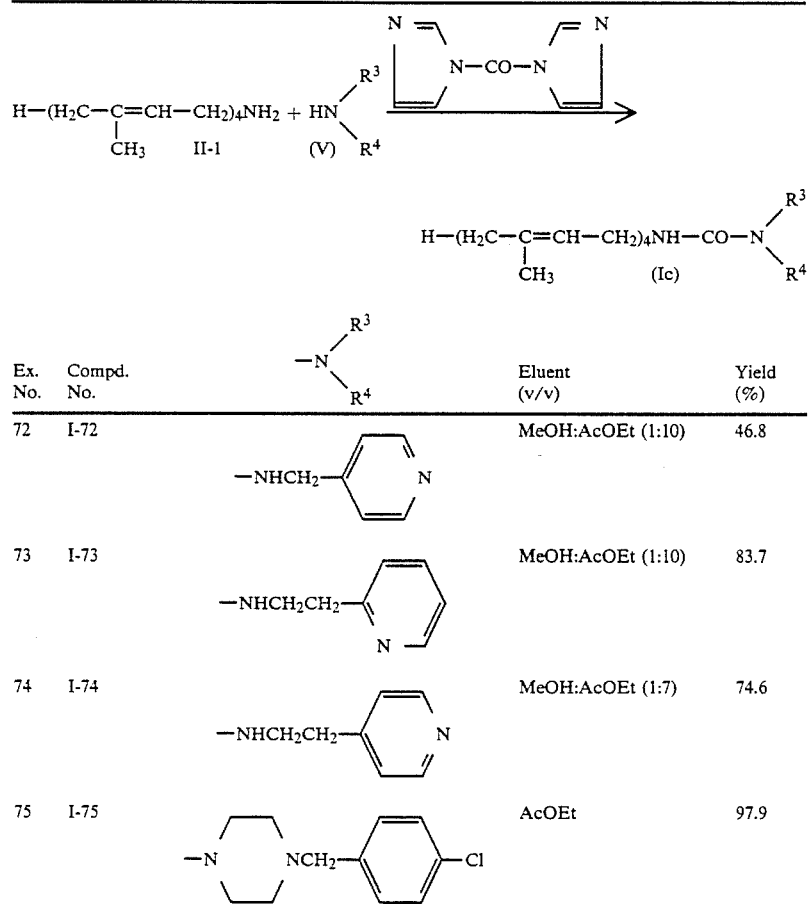

| Ex. No. | Compd. No. | $-N\begin{subarray}{l}R^3\\ R^4\end{subarray}$ | Eluent (v/v) | Yield (%) |
|---|---|---|---|---|
| 72 | I-72 | —NHCH$_2$-(4-pyridyl) | MeOH:AcOEt (1:10) | 46.8 |
| 73 | I-73 | —NHCH$_2$CH$_2$-(2-pyridyl) | MeOH:AcOEt (1:10) | 83.7 |
| 74 | I-74 | —NHCH$_2$CH$_2$-(4-pyridyl) | MeOH:AcOEt (1:7) | 74.6 |
| 75 | I-75 | —N(piperazinyl)NCH$_2$-(4-chlorophenyl) | AcOEt | 97.9 |

EXAMPLE 76

N-(3,7,11,15-Tetramethyl-2,6,10,14-hexadecatetraenyl-N'-(3-trifluoromethylphenyl)urea I-76

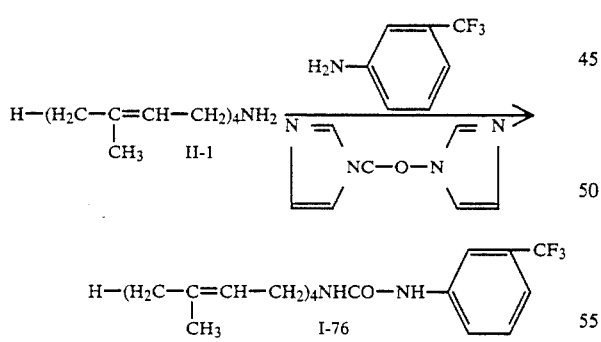

To a solution of 580 mg (2 mmol) of tetraprenylamine II-1 in 20 ml of toluene is added 357 mg (2.2 mmol) of N,N'-carbonyldiimidazole at −20° C. The mixture is stirred at the same temperature for 30 minutes and reaction temperature is returned to room temperature. The reaction mixture is mixed with 403 mg (2.5 mmol) of 3-trifluoromethylaniline and about 10 mg of p-toluene-sulfonic acid hydrate, and heated under reflux for 8 hours. After the termination of the reaction, the mixture is washed twice with 20 ml of 5% (v/v) of hydrochloric acid, twice with 20 ml of water, twice with 20 ml of saturated aqueous NaHCO$_3$, and with 20 ml of water. The resulting mixture is dried over anhydrous sodium sulfate, and evaporated under reduced pressure. The residue is purified by silica-gel column chromatography and eluted with Et$_2$O:hexane (2:1 v/v) to give 254 mg of the titled compound I-76.

Yield: 38.0%.

EXAMPLES 77–80

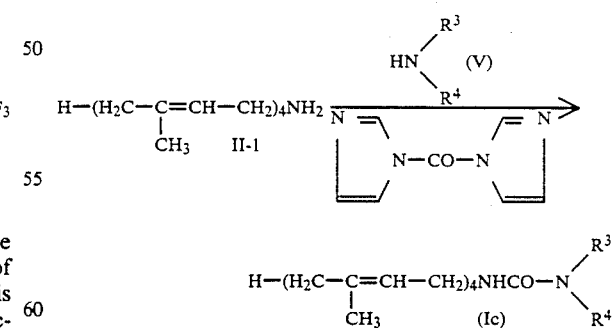

wherein $R^3$ and $R^4$ each has the same meaning as defined above.

To a solution of 580 mg (2 mmol) of tetraprenylamine II-1 in 20 ml of toluene is added 357 mg (2.2 mmol) of N,N'-carbonyl-diimidazole at −20° C. The mixture is stirred at the same temperature for 30 minutes and reaction temperature is returned to room temperature. The reaction mixture is mixed with 2.5 mmol of the compound (V) and about 10 mg of p-toluenesulfonic acid hydrate and heated under reflux for 8 hours. After the termination of the reaction, the mixture is washed twice with 20 ml of 5% (v/v) of hydrochloric acid, twice with 20 ml of water, twice with 20 ml of saturated aqueous NaHCO₃, and with 20 ml of water. The resulting mixture is dried over anhydrous sodium sulfate, evaporated under reduced pressure. The residue is purified by silica-gel column chromatography to give the objective compound (Ic).

Compound number, structural formula, and yield of the each objective compound (Ic) provided in Examples 77–80 and eluent used for silica-gel column chromatography will be shown in Table 7.

TABLE 7

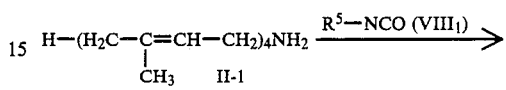

$$H-(H_2C-\underset{\underset{CH_3}{|}}{C}=CH-CH_2)_4NH_2 + HN\begin{matrix}R^3\\ \\R^4\end{matrix} \xrightarrow[\text{toluene}]{\begin{matrix}N=\\N-CO-N\\ \end{matrix}}$$

II-1 (V)

$$H-(H_2C-\underset{\underset{CH_3}{|}}{C}=CH-CH_2)_4NH-CO-N\begin{matrix}R^3\\ \\R^4\end{matrix}$$

(Ic)

| Ex. No. | Compd. No. | $-N\begin{matrix}R^3\\R^4\end{matrix}$ | Eluent (v/v) | Yield (%) |
|---|---|---|---|---|
| 77 | I-77 | —NH—⟨C₆H₄⟩—OCH₃ | Et₂O:hexane (10:1) | 50.5 |
| 78 | I-78 | —NH—⟨2-pyridyl⟩ | Et₂O | 44.5 |
| 79 | I-79 | —NH—⟨3-pyridyl⟩ | MeOH:AcOEt (1:20) | 18.1 |
| 80 | I-80 | —NH—⟨4-pyridyl⟩ | MeOH:AcOEt (1:10) | 11.0 |

EXAMPLE 81

N,N-Dimethyl-N'-(3,7,11,15-tetramethyl-2,6,10,14-hexadecatetraenyl)urea I-81

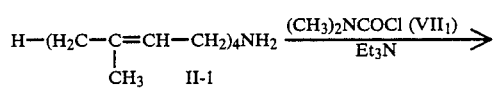

$$H-(H_2C-\underset{\underset{CH_3}{|}}{C}=CH-CH_2)_4NH_2 \xrightarrow[Et_3N]{(CH_3)_2NCOCl\ (VII_1)}$$

II-1

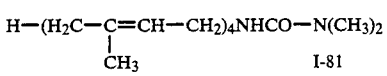

$$H-(H_2C-\underset{\underset{CH_3}{|}}{C}=CH-CH_2)_4NHCO-N(CH_3)_2$$

I-81

A mixture of 580 mg (2 mmol) of tetraprenylamine II-1, 303 mg (3 mmol) of Et₃N, and 20 ml of CH₂Cl₂ is cooled with ice-water, mixed with 269 mg (2.5 mmol) of N,N-dimethylcarbamoyl chloride, and allowed to stand at room temperature for 24 hours. The reaction mixture is washed twice with 20 ml of water, dried over anhydrous sodium sulfate, and evaporated under reduced pressure. The resulting oil is purified by silica-gel column chromatography and eluted with Et₂O:AcOEt (1:2 v/v) to give 719 mg of the titled compound as colorless oil.

Yield: 99.7%.

EXAMPLES 82–84

$$H-(H_2C-\underset{\underset{CH_3}{|}}{C}=CH-CH_2)_4NH_2 \xrightarrow{R^5-NCO\ (VIII_1)}$$

II-1

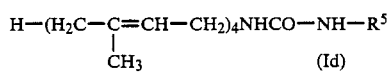

$$H-(H_2C-\underset{\underset{CH_3}{|}}{C}=CH-CH_2)_4NHCO-NH-R^5$$

(Id)

wherein R⁵ has the same meaning as defined above.

To a solution of 580 mg (2 mmol) of tetraprenylamine II-1 in 20 ml of CH₂Cl₂ is added 2.2 mmol of an isocyanate (VIII₁). The mixture is allowed to stand at room temperature for 24 hours and washed twice with 20 ml of water, dried over anhydrous sodium sulfate, and evaporated under reduced pressure. The residual oil is purified by silica-gel column chromatography and eluted with an appropriate eluent to give the objective compound (Id).

Compound number, structural formula, and yield of the each objective compound (Id) provided in Examples 82–84 and eluent used for silica-gel column chromatography will be shown in Table 8.

TABLE 8

H—(H₂C—C(CH₃)=CH—CH₂)₄NH₂ + R⁵—NCO ⟶
    II-1                            (VIII)

H—(H₂C—C(CH₃)=CH—CH₂)₄NH—CO—NH—R⁵
                                (Id)

| Ex. No. | Compd. No. | R⁵ of the compound (Id) and the compound (VIII) | Eluent (v/v) | Yield (%) |
|---|---|---|---|---|
| 82 | I-82 | —C₆H₅ (phenyl) | Et₂O:hexane (1:1) | 89.7 |
| 83 | I-83 | —C₆H₄—Cl (4-chlorophenyl) | Et₂O:hexane (2:1) | 79.3 |
| 84 | I-84 | —CH₂CH₂—(3-pyridyl) | MeOH:AcOEt (1:10) | 92.5 |

EXAMPLE 85

N-(3,7,11-Trimethyl-2,6,10-dodecatrienyl)nicotinamide I-85

H—(H₂C—C(CH₃)=CH—CH₂)₃NH₂   HOOC—(3-pyridyl)
      II-2

H—(H₂C—C(CH₃)=CH—CH₂)₃NHCO—(3-pyridyl)
                                    I-85

A mixture of 2 mmol of N-(3,7,11-trimethyl-2,6,10-dodecatrienyl)amine (hereinafter abbreviated as farnesylamine), 2.2 mmol of nicotinic acid, 562 mg (2.2 mmol) of 2-chloro-1-methylpyridinium iodide, and 444 mg (4.4 mmol) of Et₃N in 20 ml of CH₂Cl₂ is heated with stirring for 3 hours. The reaction mixture is washed twice with 20 ml of saturated aqueous NaHCO₃ and twice with 20 ml of water. The mixture is dried and evaporated under reduced pressure. The residual oil is purified by silica-gel column chromatography and eluted with AcOEt to give 426 mg of the titled compound I-85.

Yield: 65.2%.

EXAMPLE 86

N-(3,7,11-Trimethyl-2,6,10-dodecatrienyl)isonicotinamide I-86

H—(H₂C—C(CH₃)=CH—CH₂)₃NH₂ + HOOC—(4-pyridyl) ⟶

H—(H₂C—C(CH₃)=CH—CH₂)₃NHCO—(4-pyridyl)
                                    I-86

Colorless oily compound I-86 is provided in the same manner as in Example 85 from isonicotinic acid used in place of nicotinic acid.

EXAMPLE 87

1-[N-(3,7,11-Trimethyl-2,6,10-dodecatrienyl)carbamoyl]morpholine I-87

H—(H₂C—C(CH₃)=CH—CH₂)₃NH₂ + HN(morpholine) [via N,N′-carbonyldiimidazole] ⟶

H—(H₂C—C(CH₃)=CH—CH₂)₃NHCO—N(morpholine)
                                    I-87

To a solution of 442 mg (2 mmol) of farnesylamine in 20 ml of CH$_2$Cl$_2$ is added 357 mg (2.2 mmol) of N,N'-carbonyldiimidazole. The mixture is stirred at $-20°\sim 0°$ C. for 30 minutes and at a temperature of 0° C. to room temperature for 1 hour. The mixture is mixed with 218 mg (2.2 mmol) of morpholine and allowed to stand at room temperature for 24 hours. The reaction mixture is washed twice with 20 ml of water and dried over anhydrous sodium sulfate, and evaporated under reduced pressure. The residual oil is purified by silica-gel column chromatography and eluted with AcOEt to give 656 mg of the titled compound I-87.

Yield: 98.0%.

EXAMPLE 88

N-(3,7,11,15-Tetramethyl-2,6,10,14 hexadecatetraenyl)isonicotinamide I-22

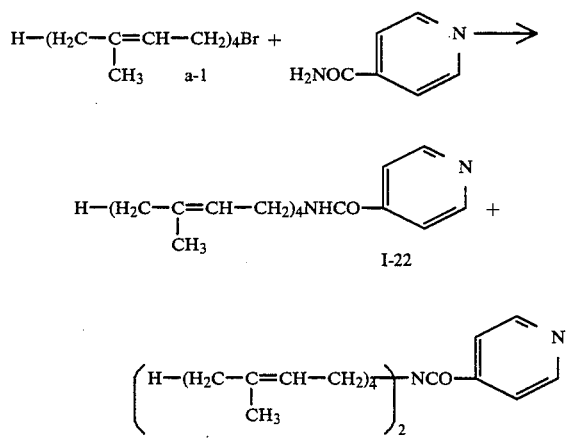

To a solution of 367 mg (3 mmol) of isonicotinamide in 20 ml of anhydrous tetrahydrofuran are added 205 mg (5 mmol) of 97% NaOH powder and 20 mg of tetra-n-butylammonium bromide. The mixture is dropwise mixed with 1.06 g (3 mmol) of tetraprenyl bromide a-1 with ice-water cooling under stirring. The reaction mixture is stirred at room temperature for 3 hours and filtered. The filtrate is concentrated under reduced pressure. The residue is extracted with 50 ml of AcOEt, washed twice with 50 ml of water, dried over anhydrous sodium sulfate, and evaporated under reduced pressure. The resulting oil is purified by silica-gel column chromatography, eluted with AcOEt and the collected preliminary fractions are concentrated to give 904 mg (yield: 44%) of N,N-bis-(3,7,11,15-tetramethyl-2,6,10,14 hexadecatetraenyl)isonicotinamide as yellowish oil.

Mass m/e (M+) 666.

IR $\nu_{max}$ (film): 1635 cm$^{-1}$.

Anal. Calcd. (for C$_{46}$H$_{70}$N$_2$O.H$_2$O) (%): C,80.65; H,10.59; N,4.09. Found (%): C,80.68; H,10.48; N,3.84.

The titled compound I-22 is eluted from the secondary fractions. Yield: 45%.

EXAMPLE 89

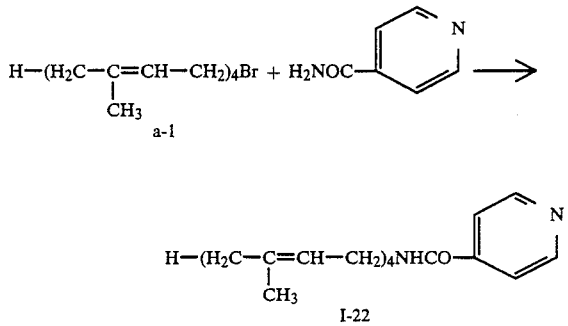

To a suspension of well-grinded mixture of 10 g of neutral alminum oxide and 3.3 g of 86% KOH in 40 ml of dioxane is added 1.22 g (10 mmol) of isonicotinamide. The mixture is mixed with 1.77 g (5 mmol) of tetraprenyl bromide a-1 and stirred at 50°$\sim$60° C. for 4 hours. The reaction mixture is filtered and concentrated under reduced pressure. The residue is extracted with 50 ml of AcOEt, washed twice with 50 ml of water, dried over anhydrous sodium sulfate, and evaporated under reduced pressure. The resulting oil is purified by silica-gel column chromatography and eluted with AcOEt to give 1.06 g of the titled compound I-22.

Yield: 54%.

EXAMPLE 90

1-(N-3,7,11,15-Tetramethyl-2,6,10,14-hexadecatetraenyl)thiocarbamoyl morpholine I-88

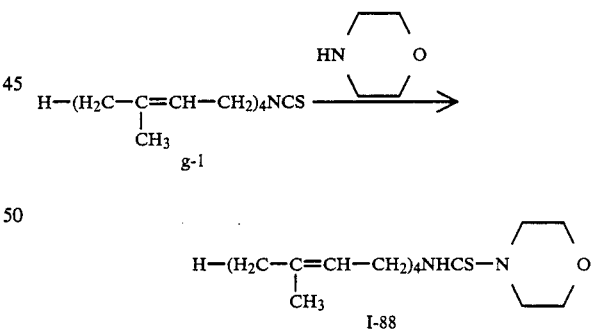

To a solution of 664 mg (2 mmol) of N-tetraprenyl isothiocyanate g-1 in 20 ml of CH$_2$Cl$_2$ is added 192 mg (2.2 mmol) of morpholine. The mixture is heated under reflux for about 2 hours. The reaction mixture is washed twice with 20 ml of water, dried over anhydrous sodium sulfate, and evaporated under reduced pressure. The residual oil is purified by silica-gel column chromatography and eluted with Et$_2$O:hexane (10:1 v/v) to give 812 mg of the objective compound I-88.

Yield: 96.9%.

EXAMPLE 91

N-(4-Pyridylmethyl)-N'-(3,7,11,15-tetramethyl-2,6,10,14-hexadecatetraenyl)thiourea I-89

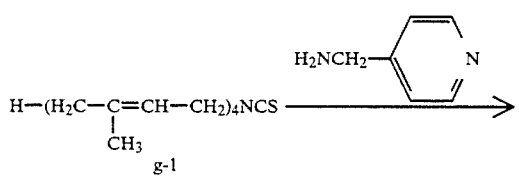

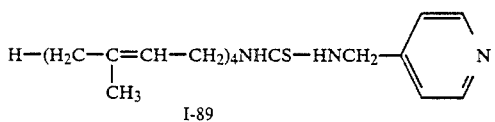

664 mg (2 mmol) of N-Tetraprenyl isothiocyanate g-1 and 238 mg (2.2 mmol) of 4-aminomethyl pyridine are allowed to react in the same manner as in Example 90 and the product is purified by silica-gel column chromatography and eluted with AcOEt:MeOH (15:1 v/v) to give 791 mg of the titled compound I-89 as yellowish oil.

Yield: 89.9%.

EXAMPLE 92

N-4-Pyridyl-N'-(3,7,11,15-tetraprenyl-2,6,10,14-hexadecatetraenyl)thiourea I-90

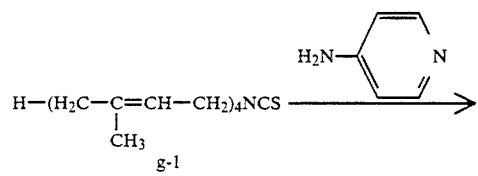

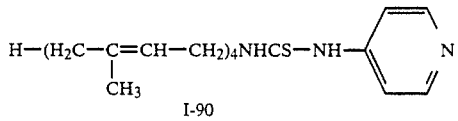

A mixture of 311 mg (3.3 mmol) of 4-aminopyridine, 10 ml of anhydrous dimethylformamide, 132 mg of NaH is stirred at room temperature for 1 hour. The mixture is mixed with 995 mg (3 mmol) of N-tetraprenyl isothiocyanate, stirred at 100° C. for another 1 hour, and concentrated under reduced pressure. The residue is extracted with 50 ml of AcOEt, washed with water (50 ml×2), dried over anhydrous sodium sulfate, and evaporated under reduced pressure. The resulting residue is purified by silica-gel column chromatography and eluted with AcOEt:MeOH (20:1 v/v) to give 815 mg of the titled compound I-90 as colorless oil.

Yield: 63.8%.

EXAMPLE 93

N-(3,7,11,15-Tetraprenyl-2,6,10,14-hexadecatetraenyl)-thionicotinamide I-91

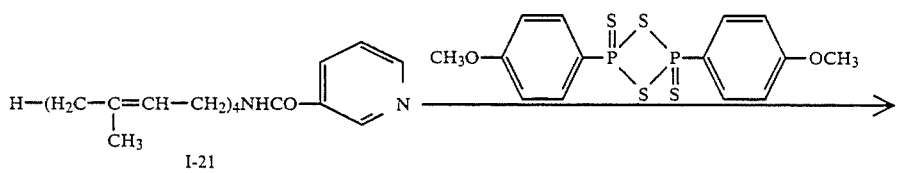

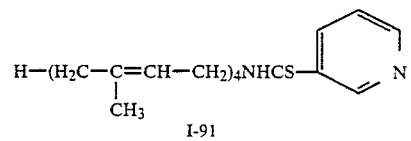

To a solution of 789 mg (2 mmol) of the compound I-21 in 20 ml of anhydrous toluene is added 1.62 g (4 mmol) of Rawesson's Reagent. The mixture is heated under reflux for 1 hour, mixed with 20 ml of saturated aqueous NaHCO₃. The reaction mixture is stirred at room temperature for 1 hour. The CH₂Cl₂ layer is washed twice with 20 ml of water, dried over anhydrous sodium sulfate, and evaporated under reduced pressure. The residual oil is purified by silica-gel column chromatography and eluted with AcOEt: Et₂O (1:2 v/v) to give 569 mg of the titled compound I-91 as yellowish oil.

Yield: 69.3%.

EXAMPLE 94

N-(3,7,11,15-Tetramethyl-2,6,10,14-hexadecatetraenyl)-thioisonicotinamide I-92

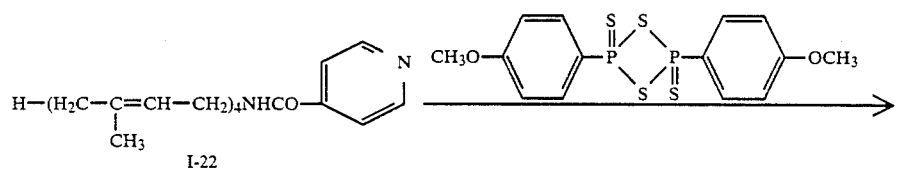

-continued

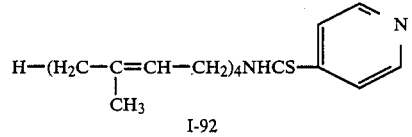

I-92

The reaction is carried out in the same manner as in Example 93 by using 737 mg (1.87 mmol) of the compound I-22, 1.54 g (3.8 mmol) of Rawesson's Reagent, and 20 ml of anhydrous toluene. The product is purified by silica-gel column chromatography and eluted with Et$_2$O:hexane (2:1 v/v) to give 585 mg of the titled compound I-92 as yellowish oil.

Yield: 76.2%.

Properties of the compounds (I) prepared in Examples will be shown in Tables 9 and 10.

TABLE 9

Properties of the compound (I)

$$H-(H_2C-\underset{\underset{CH_3}{|}}{C}=CH-CH_2)_n-NH-CX-R \quad (I)$$

(n = 4; X = O or S)

| Compd. No. | Appearance | Molecular Formula | Elemental Analysis Calcd. (%) C | H | N | Calcd. (%) C | H | N | Mass m/e(M+) | IR νmax (film) (cm$^{-1}$) CXNH | CX | NH |
|---|---|---|---|---|---|---|---|---|---|---|---|---|
| I-1 | colorless oil | C$_{21}$H$_{36}$NO.1/10H$_2$O | 78.99 | 11.11 | 4.39 | 79.00 | 11.17 | 4.38 | 317 | 1530 | 1650 | 3270 |
| I-2 | colorless oil | C$_{22}$H$_{37}$NO.1/5H$_2$O | 79.31 | 11.32 | 4.20 | 79.06 | 11.30 | 4.20 | 331 | 1550 | 1645 | 3275 |
| I-3 | colorless oil | C$_{22}$H$_{36}$NOCl.1/10H$_2$O | 71.84 Cl, 9.64 | 9.92 | 3.81 | 71.60 Cl, 9.92 | 9.90 | 3.86 | 365 (367) | 1550 | 1652 | 3275 |
| I-4 | colorless oil | C$_{23}$H$_{39}$NO$_2$.1/5H$_2$O | 75.65 | 10.88 | 3.84 | 75.81 | 10.90 | 3.92 | 345 | 1525 | 1670 | 3300 |
| I-5 | colorless oil | C$_{23}$H$_{36}$NOCl.1/5H$_2$O | 72.01 Cl, 9.24 | 10.09 | 3.65 | 72.19 Cl, 9.46 | 10.12 | 3.83 | 379 (381) | 1540 | 1640 | 3275 |
| I-6 | colorless oil | C$_{24}$H$_{40}$NOCl.H$_2$O | 69.96 | 10.27 | 3.40 | 69.78 | 9.94 | 3.53 | 393 (395) | 1540 | 1640 | 3275 |
| I-7 | colorless oil | C$_{26}$H$_{46}$NO.1/10H$_2$O | 80.19 | 11.70 | 3.60 | 80.02 | 11.66 | 3.65 | 387 | 1550 | 1643 | 3290 |
| I-8 | colorless solid (m.p. 45–50° C.) | C$_{36}$H$_{66}$NO.1/10H$_2$O | 81.62 | 12.41 | 2.64 | 81.39 | 12.51 | 2.62 | 527 | 1540 | 1635 | 3298 |
| I-9 | colorless oil | C$_{27}$H$_{39}$NO | 82.39 | 9.99 | 3.56 | 82.52 | 10.16 | 3.63 | 393 | 1540 | 1640 | 3300 |
| I-10 | colorless oil | C$_{27}$H$_{38}$NOCl | 75.76 Cl, 8.28 | 8.95 | 3.27 | 75.50 Cl, 8.38 | 8.95 | 3.39 | 427 (429) | 1540 | 1635 | 3300 |
| I-11 | colorless oil | C$_{28}$H$_{41}$NO$_2$.1/5H$_2$O | 78.71 | 9.97 | 3.28 | 78.43 | 9.71 | 3.33 | 423 | 1540 | 1625 | 3300 |
| I-12 | colorless oil | C$_{26}$H$_{37}$NO$_2$ | 78.28 | 9.72 | 3.65 | 77.95 | 9.55 | 3.82 | 383 | 1525 | 1650 | 3260 |
| I-13 | colorless oil | C$_{28}$H$_{41}$NO | 82.50 | 10.14 | 3.44 | 82.44 | 10.21 | 3.57 | 407 | 1540 | 1638 | 3260 |
| I-14 | colorless oil | C$_{28}$H$_{41}$NO$_2$ | 79.39 | 9.76 | 3.31 | 79.23 | 9.85 | 3.33 | 423 | 1520 | 1670 | 3300 |
| I-15 | colorless oil | C$_{29}$H$_{43}$NO$_2$ | 79.59 | 9.90 | 3.20 | 79.33 | 9.79 | 3.24 | 437 | 1520 | 1670 | 3300 |
| I-16 | yellowish oil | C$_{26}$H$_{41}$NO.½H$_2$O | 79.54 | 10.78 | 3.57 | 78.99 | 10.45 | 3.54 | 383 | 1545 | 1635 1665 | 3275 |
| I-17 | colorless oil | C$_{32}$H$_{63}$NO.½H$_2$O | 81.20 | 11.42 | 2.96 | 81.12 | 11.30 | 2.78 | 467 | 1540 | 1638 | 3275 |
| I-18 | yellowish oil | C$_{27}$H$_{38}$N$_2$O$_3$ | 73.94 | 8.73 | 6.39 | 73.70 | 8.75 | 6.39 | 438 | 1520 | 1635 | 3290 |
| I-19 | colorless oil | C$_{29}$H$_{44}$N$_2$O | 79.76 | 10.16 | 6.41 | 79.62 | 10.16 | 6.41 | 436 | 1505 1540 | 1605 1620 | 3300 |
| I-20 | yellowish oil | C$_{26}$H$_{38}$N$_2$O | 79.14 | 9.71 | 7.10 | 79.30 | 9.90 | 7.05 | 394 | 1515 | 1675 | 3350 |
| I-21 | yellowish oil | C$_{26}$H$_{38}$N$_2$O | 79.14 | 9.71 | 7.10 | 78.92 | 9.75 | 7.07 | 394 | 1535 | 1630 1650 | 3275 |
| I-22 | yellowish oil | C$_{26}$H$_{38}$N$_2$O | 79.14 | 9.71 | 7.10 | 79.35 | 9.85 | 7.13 | 394 | 1540 | 1640 1660 | 3300 |
| I-23 | colorless oil | C$_{26}$H$_{37}$NO$_2$ | 78.28 | 9.72 | 3.65 | 78.48 | 9.82 | 3.66 | 383 | 1530 | 1662 | 3275 |
| I-24 | colorless oil | C$_{26}$H$_{37}$NOS | 75.14 S, 8.02 | 9.33 | 3.50 | 75.11 S, 8.16 | 9.39 | 3.48 | 399 | 1540 | 1620 | 3290 |
| I-25 | colorless oil | C$_{26}$H$_{37}$NOS | 75.14 S, 8.02 | 9.33 | 3.50 | 75.31 S, 7.79 | 9.32 | 3.48 | 399 | 1540 | 1620 | 3280 |
| I-26 | colorless oil | C$_{26}$H$_{38}$N$_2$O | 78.48 | 10.01 | 7.32 | 78.25 | 10.12 | 7.38 | 382 | 1520 | 1600 1630 | 3275 |
| I-27 | colorless oil | C$_{29}$H$_{40}$N$_2$O | 80.51 | 9.32 | 6.47 | 80.54 | 9.46 | 6.56 | 432 | 1538 | 1620 | 3200 |
| I-28 | yellowish oil | C$_{26}$H$_{37}$N$_3$O | 75.91 | 9.43 | 10.62 | 75.95 | 9.56 | 10.59 | 395 | 1520 | 1670 | 3325 |
| I-29 | yellowish oil | C$_{27}$H$_{40}$N$_2$O.1/5H$_2$O | 78.67 | 9.88 | 6.80 | 78.63 | 10.16 | 6.87 | 408 | 1535 | 1640 1660 | 3260 |
| I-30 | yellowish oil | C$_{27}$H$_{40}$N$_2$O | 79.36 | 9.87 | 6.86 | 79.34 | 9.94 | 6.95 | 408 | 1540 | 1640 | 3275 |
| I-31 | yellowish oil | C$_{26}$H$_{39}$N$_2$O.½H$_2$O | 73.84 | 9.92 | 10.33 | 73.40 | 9.70 | 10.24 | 397 | 1540 | 1640 | 3200 |
| I-32 | colorless oil | C$_{34}$H$_{45}$NO | 84.42 | 9.38 | 2.90 | 84.30 | 9.49 | 3.01 | 483 | 1540 | 1635 | 3260 |
| I-33 | colorless oil | C$_{29}$H$_{41}$NO | 83.00 | 9.85 | 3.34 | 82.94 | 9.77 | 3.29 | 419 | 1540 | 1620 1655 | 3260 |
| I-34 | yellowish oil | C$_{28}$H$_{40}$N$_2$O | 79.95 | 9.59 | 6.66 | 79.56 | 9.56 | 6.59 | 420 | 1545 | 1623 1660 | 3275 |
| I-35 | yellowish oil | C$_{26}$H$_{39}$N$_3$O | 76.24 | 9.60 | 10.26 | 76.01 | 9.48 | 10.11 | 409 | 1545 | 1610 1658 | 3100 3300 |
| I-36 | colorless oil | C$_{23}$H$_{36}$N$_2$O | 77.48 | 10.18 | 7.86 | 77.28 | 10.21 | 7.94 | 356 | 1540 ν(C≡N): 2250 νmax (Nujol) | 1655 | 3280 |
| I-37 | yellowish solid | C$_{29}$H$_{42}$N$_2$O$_2$ | 77.29 | 9.39 | 6.22 | 77.00 | 9.31 | 6.27 | 450 | 1542 | 1635 | 3270 |

TABLE 9-continued

Properties of the compound (I)

$$H-(H_2C-\underset{\underset{CH_3}{|}}{C}=CH-CH_2)_n-NH-CX-R \quad (I)$$

(n = 4; X = O or S)

| Compd. No. | Appearance | Molecular Formula | Calcd. (%) C | H | N | Calcd. (%) C | H | N | Mass m/e(M+) | IR νmax (film) (cm⁻¹) CXNH | CX | NH |
|---|---|---|---|---|---|---|---|---|---|---|---|---|
| I-38 | mp. 43–48° C. colorless oil | C30H46N2O | 79.95 | 10.29 | 6.22 | 80.22 | 10.44 | 6.30 | 450 | 1515 | 1660 1678 | 3390 |
| I-39 | colorless oil | C33H42N3OF3 | 71.58 F, 10.29 | 7.65 | 7.59 | 71.80 F, 9.98 | 7.93 | 7.40 | 553 | 1520 | 1630 | 3300 |
| I-40 | yellowish solid mp 89–91° C. | C39H49N2O3Cl | 74.44 Cl, 5.63 | 7.85 | 4.45 | 74.50 Cl, 5.43 | 7.76 | 4.58 | 628 (630) | 1540 | 1630 1660 | 3290 |
| I-41 | colorless oil | C36H55NO2.1/5H2O | 80.00 | 10.63 | 2.66 | 80.11 | 10.67 | 2.75 | 521 | 1540 | 1635 | 3290 |
| I-42 | yellowish oil | C27H40N2O.½H2O | 78.21 | 9.89 | 6.76 | 78.22 | 9.84 | 6.81 | 408 | 1560 | 1620 | 3350 |
| I-43 | colorless oil | C28H42N2O.1/5H2O | 78.90 | 10.01 | 6.57 | 78.83 | 9.91 | 6.69 | 422 | 1540 | 1640 | 3280 |
| I-44 | yellowish oil | C28H42N2O.1/5H2O | 78.90 | 10.01 | 6.57 | 78.95 | 9.95 | 6.71 | 422 | 1540 | 1640 | 3275 |
| I-45 | colorless oil | C33H61NO | 82.96 | 10.76 | 2.93 | 82.95 | 11.04 | 2.97 | 477 | 1540 | 1640 | 3275 |
| I-46 | colorless oil | C29H41NO3.1/10H2O | 76.81 | 9.16 | 3.09 | 76.79 | 9.18 | 3.13 | 451 | 1520 | 1640 1760 | 3300 |
| I-47 | colorless oil | C28H42N2O.1/5H2O | 78.90 | 10.01 | 6.57 | 78.82 | 10.03 | 6.59 | 422 | 1540 | 1640 | 3270 |
| I-48 | colorless oil | C26H46N2O | 77.55 | 11.52 | 6.96 | 77.44 | 11.58 | 6.93 | 402 | 1510 | 1670 1680 | 3350 |
| I-49 | colorless oil | C26H44N2O2.¼H2O | 74.15 | 10.65 | 6.65 | 74.21 | 10.43 | 6.60 | 416 | 1505 | 1670 | 3300 |
| I-50 | yellowish oil | C31H48N4O.1/10H2O | 75.29 | 9.82 | 11.33 | 75.12 | 9.99 | 11.20 | 492 | 1520 | 1680 | 3350 |
| I-51 | colorless oil | C25H39N3O.1/5H2O | 74.84 | 9.89 | 10.57 | 74.46 | 9.84 | 10.35 | 397 | 1550 | 1660 | 3275 |
| I-52 | yellowish oil | C29H52N2O.½H2O | 76.25 | 11.70 | 6.13 | 76.02 | 11.51 | 6.34 | 447 | 1540 | 1645 | 3275 |
| I-53 | yellowish oil | C28H60N2O | — | — | — | — | — | — | 433 | 1540 | 1645 | 3275 |
| I-54 | colorless oil | C24H37N3O | 75.15 | 9.72 | 10.95 | 75.03 | 9.66 | 10.73 | 383 | 1540 | 1695 1725 | 3200 |
| I-55 | colorless oil | C25H42N2O2 | 74.58 | 10.51 | 6.96 | 74.18 | 10.42 | 6.89 | 402 | 1540 | 1620 | 3325 |
| I-56 | colorless oil | C26H44N2O | 77.95 | 11.07 | 6.99 | 77.61 | 11.15 | 6.91 | 400 | 1537 | 1620 | 3320 |
| I-57 | colorless solid (mp. 41–48° C.) | C21H36N2O | 75.85 | 10.91 | 8.42 | 75.71 | 10.83 | 8.44 | 332 | νmax (Nujol) 1558 | 1645 | 3325 |
| I-58 | colorless oil | C28H47N3O3 | 71.00 | 10.00 | 8.87 | 70.92 | 10.15 | 8.66 | 473 | 1530 | 1620 1697 | 3325 |
| I-59 | colorless oil | C26H46N3O | 75.13 | 10.91 | 10.11 | 74.87 | 10.97 | 10.09 | 415 | 1535 | 1620 | 3320 |
| I-60 | colorless oil | C31H47N3O | 77.94 | 9.92 | 8.80 | 78.20 | 9.85 | 8.65 | 477 | 1535 | 1620 | 3320 |
| I-61 | colorless oil | C30H46N4O | 75.27 | 9.69 | 11.70 | 75.21 | 9.62 | 11.51 | 478 | 1530 | 1620 | 3325 |
| I-62 | colorless oil | C33H49N3O3.1/10H2O | 73.73 | 9.23 | 7.82 | 73.53 | 9.23 | 7.82 | 535 | 1540 | 1620 | 3325 |
| I-63 | colorless oil | C26H45N3O | 74.39 | 11.24 | 10.41 | 74.13 | 11.19 | 10.32 | 403 | 1570 | 1630 | 3325 |
| I-64 | yellowish oil | C27H47N3O3 | 72.76 | 10.63 | 9.43 | 72.35 | 10.64 | 9.65 | 445 | 1560 | 1620 | 3325 |
| I-65 | yellowish oil | C28H49N3O2.½H2O | 71.75 | 10.75 | 8.96 | 71.90 | 10.58 | 9.30 | 459 | 1568 | 1625 | 3325 |
| I-66 | colorless oil | C28H42N2O | 79.57 | 10.02 | 6.63 | 79.57 | 10.17 | 6.42 | 422 | 1570 | 1630 | 3325 |
| I-67 | colorless solid (mp. 67–75° C.) | C28H41N2OCl | 73.57 Cl, 7.76 | 9.04 | 6.13 | 73.50 Cl, 7.54 | 9.06 | 6.13 | 456 (458) | 1580 | 1615 | 3320 |
| I-68 | colorless oil | C29H42N2O3 | 74.64 | 9.07 | 6.00 | 74.62 | 9.13 | 6.10 | 466 | 1570 | 1610 | 3300 |
| I-69 | colorless oil | C29H44N2O | 79.76 | 10.16 | 6.41 | 79.66 | 10.39 | 6.35 | 436 | 1570 | 1625 | 3325 |
| I-70 | colorless solid (mp. 69–74° C.) | C27H41N3O | 76.55 | 9.76 | 9.92 | 76.40 | 9.87 | 9.96 | 423 | νmax (Nujol) 1520 | 1620 | 3325 |
| I-71 | yellowish oil | C27H41N3O.½H2O | 74.96 | 9.79 | 9.71 | 75.19 | 9.59 | 9.86 | 423 | 1565 | 1635 | 3320 |
| I-72 | colorless solid (mp. 41–47° C.) | C27H41N3O.1/6H2O | 76.01 | 9.77 | 9.85 | 76.01 | 9.83 | 10.06 | 423 | νmax (Nujol) 1550 | 1610 | 3280 |
| I-73 | colorless oil | C28H43N3O.⅔H2O | 74.79 | 9.94 | 9.94 | 74.65 | 9.67 | 9.37 | 437 | 1560 | 1620 | 3310 |
| I-74 | colorless oil | C28H43N3O.½H2O | 75.29 | 9.93 | 9.41 | 75.54 | 9.74 | 9.44 | 437 | 1560 | 1635 | 3320 |
| I-75 | yellowish oil | C32H48N3O.Cl.¼H2O | 72.42 Cl, 6.68 | 9.21 | 7.92 | 72.35 Cl, 6.42 | 9.26 | 8.05 | 525 | 1540 | 1615 | 3325 |
| I-76 | colorless oil | C28H39N2OF3 | 70.56 F, 11.96 | 8.25 | 5.88 | 70.46 F, 11.74 | 8.36 | 5.77 | 476 | 1555 | 1640 | 3300 |
| I-77 | colorless solid (mp. 48–60° C.) | C28H42N2O2 | 76.67 | 9.65 | 6.39 | 77.11 | 9.89 | 6.03 | 438 | νmax (Nujol) 1505 1570 | 1630 | 3310 |
| I-78 | colorless oil | C26H39N3O | 76.24 | 9.60 | 10.26 | 76.18 | 9.62 | 10.04 | 409 | 1540 | 1675 | 3100 3200 |
| I-79 | colorless oil | C26H39N3O.4/5H2O | 73.65 | 9.65 | 9.91 | 73.70 | 9.38 | 9.91 | 409 | 1550 | 1655 | 3325 |
| I-80 | colorless solid (mp. 50–62° C.) | C26H39N3O.5/2H2O | 68.69 | 9.75 | 9.24 | 68.57 | 8.66 | 9.31 | 409 | νmax (Nujol) 1530 | 1670 | 3275 |
| I-81 | colorless oil | C23H40N2O.1/10H2O | 76.23 | 11.18 | 7.73 | 76.07 | 11.22 | 7.72 | 360 | 1535 | 1640 | 3325 |
| I-82 | colorless oil | C27H40N2O | 79.36 | 9.87 | 6.86 | 79.46 | 9.88 | 6.93 | 408 | 1555 | 1643 | 3325 |
| I-83 | colorless solid (mp. 81–84° C.) | C27H39N2OCl | 73.19 Cl, 8.00 | 8.87 | 6.32 | 73.11 Cl, 8.06 | 8.76 | 6.35 | 442 (444) | 1560 | 1620 | 3280 |
| I-84 | colorless oil | C28H43N3O.3/2H2O | 72.37 | 9.97 | 9.04 | 72.31 | 9.27 | 9.13 | 437 | 1540 | 1640 | 3260 |
| I-88 | colorless oil | C26H42N2OS.1/10H2O | 71.41 S, 7.62 | 10.12 | 6.66 | 71.22 S, 7.53 | 10.16 | 6.78 | 418 | 1520 | 1115 | 3280 |
| I-89 | colorless oil | C27H41N3S.1/10H2O | 73.45 S, 7.26 | 9.41 | 9.52 | 73.36 S, 7.17 | 9.34 | 9.49 | 439 | 1540 | — | 3230 |
| I-90 | yellowish oil | C26H39N3S.1/5H2O | 72.75 S, 7.47 | 9.25 | 9.79 | 72.56 S, 7.36 | 9.20 | 9.68 | 425 | 1500 1520 | 1215 | 3180 3280 |
| I-91 | yellow oil | C26H38N2S.1/10H2O | 75.71 | 9.34 | 6.79 | 75.49 | 9.32 | 6.79 | 410 | 1520 | 1100 | 3175 |

TABLE 9-continued

Properties of the compound (I)

$$\text{H—(H}_2\text{C—C(CH}_3\text{)=CH—CH}_2)_n\text{—NH—CX—R} \quad (I)$$

(n = 4; X = O or S)

| Compd. No. | Appearance | Molecular Formula | Elemental Analysis Calcd. (%) C H N | Calcd. (%) C H N | Mass m/e(M+) | IR νmax (film) (cm⁻¹) CXNH | CX | NH |
|---|---|---|---|---|---|---|---|---|
| I-92 | yellow oil | C$_{26}$H$_{38}$N$_2$S.½H$_2$O | S, 7.77<br>75.22  9.35  6.75<br>S, 7.72 | S, 8.01<br>75.01  9.29  6.62<br>S, 8.24 | 410 | 1520 | 1098 | 3175 |

TABLE 10

$$\text{H(H}_2\text{C—C(CH}_3\text{)=CH—CH}_2)_n\text{—NH—CO—R} \quad (I)$$

(n = 3)
Properties of the compound (I)

| Compd. No. | Appearance | Molecular Formula | Calcd. (%) C H N | Found (%) C H N | Mass m/e(M+) | IR ν max(film)(cm⁻¹) CONH | CO | NH |
|---|---|---|---|---|---|---|---|---|
| I-85 | colorless oil | C$_{21}$H$_{30}$N$_2$O | 77.26  9.26  8.58 | 77.38  9.29  8.55 | 326 | 1540 | 1635<br>1660 | 3300 |
| I-86 | colorless oil | C$_{21}$H$_{30}$N$_2$O | 77.26  9.26  8.58 | 76.83  9.10  8.49 | 326 | 1540 | 1640 | 3280 |
| I-87 | colorless oil | C$_{20}$H$_{34}$N$_2$O$_2$ | 71.81  10.25  8.37 | 71.71  10.26  8.26 | 334 | 1540 | 1625 | 3325 |

EXAMPLE 95

N-[E,E,E]-Tetraprenylisonicotinamide I-22-1

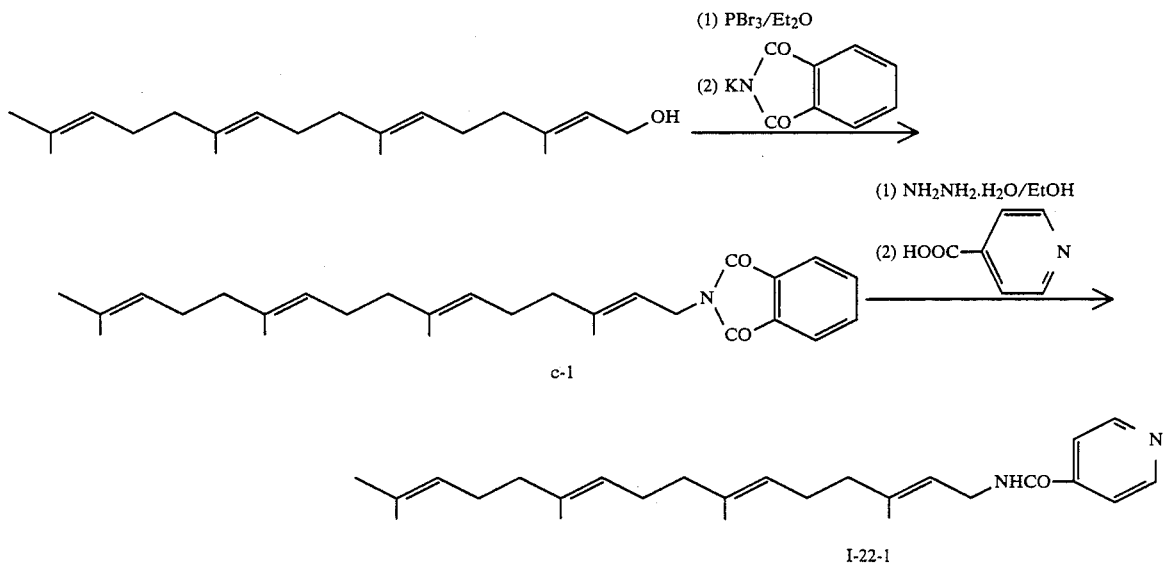

c-1

I-22-1

To a stirred solution of 2.90 g (10 mmol) of [E,E,E]-geranylgeraniol in 50 ml of anhydrous Et$_2$O are added 1 drop of pyridine at −20° ∼ −25° C. under nitrogen gas flow and a solution of 5 mmol of phosphorus tribromide in 10 ml of anhydrous Et$_2$O in about 5 minutes. The mixture is stirred for 30 minutes at the same temperature and the reaction mixture is stirred until the reaction temperature is returned to the room temperature. After 1 hour, the reaction mixture is cooled with ice-water, mixed with 50 ml of water. The product is extracted with 100 ml of hexane, washed twice with 100 ml of water, dried over anhydrous sodium sulfate, and evaporated under reduced pressure. The resulting oil is dissolved in 10 ml of anhydrous tetrahydrofuran. The solution is added to a suspension of 1.85 g (10 mmol) of potassium phthalimide and 50 mg of tetra-n-butylammonium bromide in 100 ml of anhydrous tetrahydrofuran with stirring at room temperature. The mixture is heated under reflux for 3 hours. The reaction mixture is filtered and concentrated under reduced pressure. The residue is purified by silica-gel column chromatography and eluted with Et$_2$O:hexane (1:2 v/v) to give 3.58 g of N-[E,E,E]-tetraprenyl phthalimide c-1 as yellowish oil.
Yield: 85.3%.

The compound c-1 is dissolved in 100 ml of anhydrous alcohol, mixed with 1 g (20 mmol) of 100% hydrazine hydrate, and heated under reflux for 3 hours. The reaction mixture is filtered, and the filtrate is concentrated under reduced pressure. The resulting residue is extrated with 100 ml of a mixture of $Et_2O$: hexane (1:1 v/v). The extract is washed with 5% aqueous NaOH (100 ml×2) and water (100 ml×2), dried over anhydrous sodium sulfate, and evaporated under reduced pressure to give 2.46 g of [E,E,E]-tetraprenylamine. II-1-1.

To 50 ml of a solution of 1.09 g (9 mmol) of isonicotinic acid in anhydrous $CH_2Cl_2$ are added 1.01 g (10 mmol) of $Et_3N$ with ice-cooling and 977 mg (9 mmol) of ethyl chlorocarbonate. The mixture is stirred at room temperature for 2 hours, mixed with 10 ml of a solution of 2.46 g of [E,E,E]-tetraprenylamine in $CH_2Cl_2$, and stirred at room temperature for 2 hours. The mixture is washed with water (50 ml×2), dried over anhydrous sodium sulfate, and evaporated under reduced pressure. The residual oil is purified by silica-gel column chromatography and eluted with AcOEt to give 2.65 g of the objective compound I-22-1.

Yield: 67.2%.

EXAMPLES 96–102

Stereoisomers prepared in the same manner as in Example 95 will be shown in Table 11.

TABLE II

| Ex. Nos. | Compd. Nos. | steric configuration | Yield (%) |
|---|---|---|---|
| 96 | I-22-2 | Z,E,E | 67.5 |
| 97 | I-22-3 | E,E,Z | 62.6 |
| 98 | I-22-4 | Z,E,Z | 41.8 |
| 99 | I-22-5 | Z,Z,Z | 67.5 |
| 100 | I-22-6 | Z,Z,E | 59.6 |
| 101 | I-22-7 | E,Z,Z | 65.4 |
| 102 | I-22-8 | E,Z,E | 54.9 |

$^{13}$C-NMR Data of the compounds I-22-1 ~ I-22-8 will be summarized in Table 12.

TABLE 12

The $^{13}$C—NMR Chemical Shift Data [δ ($CDCl_3$)ppm] of Each Stereoisomers of N-Tetraprenylisonicotinamide (25.2 MHz, TMS Internal Standard)

| | E,E,E | Z,E,E | E,E,Z | Z,E,Z | Z,Z,Z | Z,Z,E | E,Z,Z | E,Z,E |
|---|---|---|---|---|---|---|---|---|
| α | 150.36 | 150.41 | 150.52 | 150.48 | 150.51 | 150.51 | 150.53 | 150.55 |
| β | 121.06 | 120.97 | 120.92 | 120.97 | 120.88 | 120.86 | 120.88 | 120.88 |
| γ | 119.32 | 120.04 | 119.19 | 120.07 | 120.04 | 120.01 | 119.17 | 119.18 |
| C=O | 165.39 | 165.32 | 165.32 | 165.33 | 165.27 | 165.25 | 165.30 | 165.31 |
| $C_1$ | 38.19 | 38.02 | 38.20 | 38.02 | 37.94 | 37.93 | 38.17 | 38.17 |
| $C_2,C_3$ | (141.91 / 140.62) | (141.88 / 141.04) | (141.84 / 141.06) | (141.88 / 141.10) | (141.79 / 141.09) | (141.25 / 141.09) | (141.81 / 141.00) | (141.80 / 140.02) |
| $C_7,C_{11}$ | (135.50 / 134.99) | (135.98 / 135.10) | (135.55 / 135.21) | (135.96 / 135.26) | (136.05 / 135.49) | (136.15 / 135.33) | (135.65 / 135.42) | (135.75 / 135.29) |
| $C_6,C_{10},C_{14}$ | (124.40 / 124.13 / 123.64) | (124.39 / 124.05 / 123.39) | (124.95 / 124.40 / 123.66) | (124.88 / 124.41 / 123.45) | (124.82 / 124.26) | (124.29 / 124.16 / 123.95) | (124.94 / 124.40 / 124.32) | (124.37 / 124.20 / 124.08) |
| $C_{15}$ | 131.20 | 131.23 | 131.51 | 131.49 | 131.57 | 131.35 | 131.55 | 131.29 |
| $C_{16}$ | 25.68 | 25.69 | 25.73 | 25.73 | 25.72 | 25.70 | 25.70 | 25.69 |
| $C_{20}$ | 17.67 | 17.67 | 17.64 | 17.64 | 17.66 | 17.69 | 17.63 | 17.69 |
| $C_5,C_9,C_{13}$ | (26.78 / 26.66 / 26.34) | (26.79 / 26.63 / 26.49) | (26.66 / 26.57 / 26.33) | (26.65 / 26.50) | (26.48 / 26.36 / 26.24) | (26.71 / 26.53 / 26.23) | (26.70 / 26.37 / 26.18) | (26.75 / 26.55 / 26.19) |
| $C_4,C_8,C_{12}$ | (39.72 / 39.55) | 32.09 / 39.75 / 39.75 | (43.03 / 39.55) 32.03 | 32.05 / 40.10 / 32.05 | (32.25 / 31.99) | (32.25 / 31.94) 39.74 | 39.80 (32.30 / 31.99) | (39.77) 32.00 (39.55) |
| $C_{17},C_{18},C_{19}$ | (16.39 / 16.01) | 23.44 / 16.04 / 16.04 | (16.34 / 16.07) 23.41 | 23.41 / 16.04 / 23.41 | 23.41 / 23.41 / 23.41 | 23.46 / 23.46 / 15.99 | 16.41 / 23.41 / 23.41 | (16.43) 23.42 (16.01) |

(Unassignable signals are in parentheses)

EXAMPLE 103

A complex of the compound I-21 and β-cyclodextrin

A mixture (30 ml) of 197 mg (0.5 mmol) of the compound I-21 in alcohol is added to 50 ml of an aqueous solution of 1.70 g (1.5 mmol) of β-cyclodextrin at room temperature with stirring. The mixture is stirred for 24 hours, and the white precipitate is filtered and washed with 50 ml of alcohol. The resulting white powder is dried over phosphorus pentoxide in desiccator for 3 days to give 1.79 g of the objective complex X II-1 as white powder.

EXAMPLES 104–106

A complex of the compounds I-22, 42, and 93; and β-cyclodextrin is prepared in the same manner as in Example 103.

EXAMPLE 107

A complex of the compound I-22 and γ-cyclodextrin

A mixture (30 ml) of 197 mg (0.5 mmol) of the compound I-22 in alcohol is added to 30 ml of an aqueous solution of 1.95 g (1.5 mmol) of γ-cyclodextrin at room temperature with stirring. The reaction mixture is stirred at room temperature for 24 hours, the resulting white precipitate is filtered and washed with 50 ml of alcohol. The resulting white powder is dried over phosphorus pentoxide in desiccator for 3 days to give 1.78 g of the objective complex X II-5 as white powder.

EXAMPLES 108–109

A complex of the compound I-21 and 42; and γ-cyclodextrin is prepared in the same manner as in Example 107.

Molecular formulae, appearance, yield, and elemental analyses of complexes X II prepared in Examples 103–109 will be shown in Tables 13 and 14.

TABLE 13

$$H-(H_2C-\underset{CH_3}{\underset{|}{C}}=CH-CH_2)_4-NH\underset{X}{\underset{\|}{C}}-R \quad \text{Cyclodextrin Complex}$$

| Compd. Nos. | R | X | cyclo-dextrin | Appearance | Yield (%) |
|---|---|---|---|---|---|
| X II-1 | 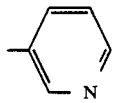 | O | β | white powder | 77.0 |
| X II-2 | 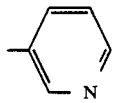 | O | β | white powder | 87.8 |
| X II-3 | —CH2—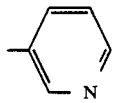 | O | β | white powder | 79.8 |
| X II-4 | 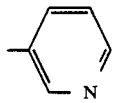 | S | β | yellowish powder | 59.6 |
| X II-5 | 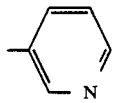 | O | γ | white powder | 81.2 |
| X II-6 | 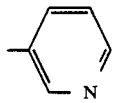 | O | γ | white powder | 70.8 |
| X II-7 | —CH2—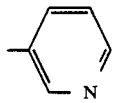 | O | γ | white powder | 72.7 |

TABLE 14

| Compd. Nos. | Molecular Composition | Calcd. (%) C | H | N | H2O | Found (%) C | H | N | H2O |
|---|---|---|---|---|---|---|---|---|---|
| X II-1 | [C26H38N2O][3.4β-CD][22H2O] | 43.60 | 6.94 | 0.60 | 8.52 | 43.90 | 6.87 | 0.82 | 8.77 |
| X II-2 | [C26H38N2O][3.2β-CD][21H2O] | 43.74 | 6.96 | 0.64 | 8.59 | 43.96 | 6.92 | 0.82 | 8.33 |
| X II-3 | [C27H41N3O][3.0β-CD][3H2O] | 47.33 | 6.67 | 1.08 | 1.39 | 47.25 | 6.73 | 1.35 | 2.39 |
| X II-4 | [C26H38N2S][3.0β-CD][16H2O] | 44.49 | 6.88 | 0.68 | | 44.41 | 6.69 | 0.68 | |
| | | S,0.78 | | | | S,0.88 | | | |
| X II-5 | [C26H38N2O][3.0γ-CD][5H2O] | 46.66 | 6.63 | 0.64 | 2.06 | 46.56 | 6.98 | 0.74 | 1.87 |
| X II-6 | [C26H38N2O][3.0γ-CD][15H2O] | 44.81 | 6.86 | 0.61 | | 44.74 | 6.96 | 0.59 | |
| X II-7 | [C27H41N3O][3.0γ-CD][15H2O] | 45.15 | 6.80 | 0.92 | | 45.00 | 6.96 | 0.90 | |

CD: Cyclodextrin

REFERENTIAL EXAMPLE 1

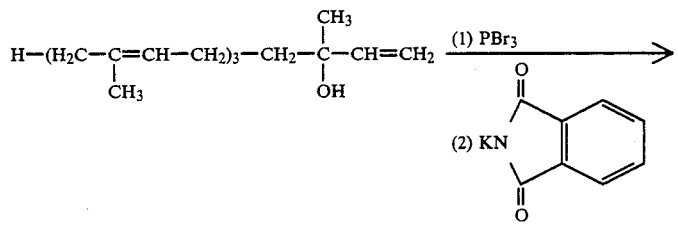

$$H-(H_2C-\underset{\underset{CH_3}{|}}{C}=CH-CH_2)_4-N\underset{CO}{\overset{CO}{\diagdown}}\!\!\!\bigcirc \xrightarrow{NH_2NH_2 \cdot H_2O} H-(H_2C-\underset{\underset{CH_3}{|}}{C}=CH-CH_2)_4NH_2$$

c-1 → II-1

(1) N-(3,7,11,15-Tetramethyl-2,6,10,14-hexadecatetraenyl)-phthalimide c-1

To 100 ml of a stirred solution of 14.5 g (50 mmol) of geranyl-linalol and 0.5 ml of pyridine in anhydrous Et$_2$O is dropwise added 20 ml of a solution of 5.2 g (19.2 mmol) of phosphorus tribromide in anhydrous Et$_2$O at $-20° \pm 5°$ C. The mixture is stirred for 30 minutes at the same temperature, at 0° C. for 2 hours, and at room temperature for 30 minutes. The reaction mixture is mixed with 200 ml of hexane and 200 ml of water in order under cooling. The organic layer is collected by filtration, washed twice with water (200 ml×2), dried over anhydrous sodium sulfate, and evaporated under reduced pressure to give 17.5 g (yield: 99.0%) of tetraprenyl bromide as yellowish oil.

The oil is dissolved in 100 ml of N,N-dimethylformamide, mixed with 9.26 g (50 mmol) of anhydrous potassium phthalimide, and stirred at 50°~60° C. for 3 hours. The reaction mixture is filtered, and the filtrate is concentrated under reduced pressure. The residue is mixed with 200 ml of hexane, washed twice with 100 ml of 10% acetic acid and twice with 200 ml of water, dried over anhydrous sodium sulfate, and evaporated under reduced pressure to give 19.9 g (yield: 95.0%) of the titled compound c-1 as yellowish oil. This is purified by silica-gel column chromatography and eluted with hexane: Et$_2$O (2:1 v/v) to give 14.7 g (yield: 70.7%) of the authentic specimen of the compound c-1 as colorless oil.

Mass: m/e (M+) 419.
IR $\nu_{max}$(film): 1705, 1762 cm$^{-1}$.

(2) 3,7,11,15-Tetramethyl-2,6,10,14-hexadecatetraenylamine: (Tetraprenylamine) II -1

14.2 g (33.8 mmol) of the compound c-1 provided above step (1) is dissolved in 200 ml of anhydrous EtOH. To the solution is added 3.4 g (68 mmol) of 100% hydrazine hydrate. The mixture is heated under reflux and filtered. The filtrate is concentrated under reduced pressure, the resulting oil is evaporated to give 7.35 g (yield: 75.0%) of the titled compound II-1 as colorless oil.

Boiling point (0.75 mmHg): 141°~142° C.
Mass: m/e (M+) 289.
IR $\nu_{max}$(film): 3250, 3340 cm$^{-1}$.

REFERENTIAL EXAMPLE 2

$$H-(H_2C-\underset{\underset{CH_3}{|}}{C}=CH-CH_2)_3-CH_2-\underset{\underset{OH}{|}}{\overset{\overset{CH_3}{|}}{C}}-CH=CH_2 \xrightarrow[(2) NaN_3]{(1) PBr_3}$$

$$H-(H_2C-\underset{\underset{CH_3}{|}}{C}=CH-CH_2)_4N_3 \xrightarrow{LiAlH_4}$$
d-1

$$H-(H_2C-\underset{\underset{CH_3}{|}}{C}=CH-CH_2)_4NH_2$$
II-1

(1) 3,7,11,15-Tetrametyl-2,6,10,14-hexadecatetraenylazide d-1

To a solution of 19.9 g of tetraprenyl bromide provided in Referential Example 1 in 100 ml of anhydrous tetrahydrofuran are added 3.9 g (60 mmol) of sodium azide and 250 mg of tetra-(n-butyl)ammonium bromide. The mixture is heated under reflux for 5 hours and filtered. The filtrate is concentrated under reduced pressure. The residue is dissolved in 200 ml of Et$_2$O:hexane and washed 3 times with 100 ml of water. The organic layer is dried over anhydrous sodium sulfate and evaporated under reduced pressure to give 15.7 g (yield: 99.5%) of the titled compound d-1 as yellowish or yellow oil.

IR $\nu_{max}$(film): 2090 cm$^{-1}$.

(2) Tetraprenylamine II -1

To 200 ml of a suspension of 417 mg (11 mmol) of lithium aluminum hydride in anhydrous Et$_2$O is dropwise added 20 ml of a solution of 3.15 g (10 mmol) of the azide provided in above step (1) in anhydrous Et$_2$O at $-10°$~$-15°$ C. under cooling with stirring for about 10 minutes. The mixture is stirred at $-5°$ C. for 2 hours and at room temperature for another 1 hour. The mixture is mixed with 100 ml of 10% aqueous sodium hydroxide with stirring. The Et$_2$O layer is collected and washed with water (100 ml ×2). The resulting mixture is dried over ahydrous sodium sulfate and evaporated under reduced pressure. The residual oil is purified by silica-gel column chromatography and eluted with NH$_4$OH:MeOH (5:95 v/v) to give 2.21 g (yield: 76.7%) of the titled compound II -1.

This is identified with tetraprenylamine provided in Referential Example 1-(2).

REFERENTIAL EXAMPLE 3

$$H-(H_2C-\underset{\underset{CH_3}{|}}{C}=CH-CH_2)_4Br \xrightarrow[NH_3]{NaNH_2}$$
a-1

$$H-(H_2C-\underset{\underset{CH_3}{|}}{C}=CH-CH_2)_4NH_2$$
II-1

A mixture of 3.53 g (10 mmol) of tetraprenyl bromide a-1 prepared in Referential Example 1 and 780 mg (20 mmol) of sodium amide is dissolved in 10 ml of liquid ammonia and allowed to stand at room temperature for 2 days in a sealed tube. After termination of the reaction, the tube is opened and ammonia is evaporated. The residue is washed with 100 ml of hexane, the material soluble in hexane is washed with water (100 ml ×2), dried over anhydrous sodium sulfate, and evaporated. The residual oil is purified by silica-gel column chromatography and eluted with NH$_4$OH:MeOH (5:95 v/v) to give 1.07 g (yield: 37%) of tetraprenylamine II -1.

This is identified with tetraprenylamine provided in Referential Example 1-(2).

REFERENTIAL EXAMPLE 4

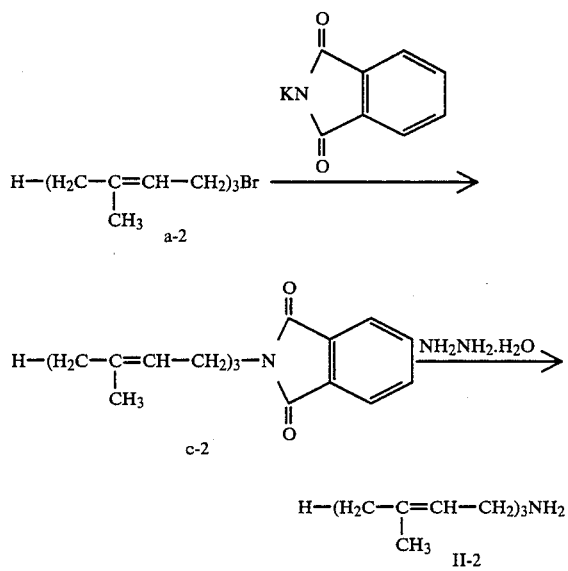

(1) N-(3,7,11,15-Trimethyl-2,6,10-dodecatrienyl)phthalimide c-2

A mixture of 11.41 g (40 mmol) of farnesyl bromide a-2 and 7.41 g (40 mmol) of potassium phthalimide is heated at 50°~60° C. in 50 ml of N,N-dimethylformamide with stirring for 3 hours. The reaction mixture is filtered. The filtrate is concentrated under reduced pressure. The residue is mixed with 200 ml of hexane, washed with 10% aqueous acetic acid (100 ml ×2) and with water (100 ml ×2), dried over anhydrous sodium sulfate, and evaporated under reduced pressure. The residual oil is purified by silica-gel column chromatography to give 9.56 g (yield: 680%) of the titled compound c-2 as colorless oil.

Mass: m/e (M+) 351.

IR $\nu_{max}$ (film): 1705, 1762 cm$^{-1}$.

(2) N-(3,7,11-Trimethyl-2,6,10-dodecatrienyl)amine: (Farnesylamine) II-2

A solution of 9.56 g (27 mmol) of the compound c-provided in the above step (1) in 200 ml of anhydrous EtOH is mixed with 2.7 g (54 mmol) of 100% hydrazine hydrate and heated under reflux. The reaction mixture is filtered, and the fltrate is concentrated. The residual oil is evaporated under reduced pressure to give 4.72 g (yield: 78.9%) of the titled compound II-2 as colorless oil. Boiling point (0.8 mmHg): 108°~109° C.

REFERENTIAL EXAMPLE 5

N-(3,7,11,15-Tetramethyl-2,6,10,14-hexadecatetraenyl)isothiocyanate IX-1

H—(H$_2$C—C(CH$_3$)=CH—CH$_2$)$_4$NH$_2$ ⟶
    II-1

H—(H$_2$C—C(CH$_3$)=CH—CH$_2$)$_4$NCS
    IX-1

To a mixture of 8.69 g (30 mmol) of tetraprenylamine II-1, 300 ml of anhydrous dichloromethane, and 12.6 ml of triethylamine is added 15 ml of carbon disulfide with ice-water cooling. The mixture is stirred at room temperature for 2 hours, and the reaction mixture is cooled with ice-water and mixed with 3.15 ml (33 mmol) of ethyl chlorocarbonate. The reaction mixture is stirred at the same temperature for 2 hour then at room temperature for 1 hour. The resulting mixture is washed with water (300 ml×2), dried over anhydrous sodium sulfate, and evaporated under reduced pressure. The residual oil is purified by silica-gel column chromatography and eluted with Et$_2$O:hexane (1:10 v/v) to give 9.37 g of the titled compound IX-1 as yellowish liquid.

Yield: 94.2%.

The compound IX-1 is also prepared by using 33 mmol of 1-methyl-2-chloropyridinium iodide in place of ethyl chlorocarbonate.

IR $\nu_{max}$ (film): 2012, 2080 cm$^{-1}$.

Mass m/e(M+) 331.

Anal. Calcd. (for C$_{21}$H$_{33}$NS) (%) C,76.07; H,10.03; N,4.22; S,9.67. Found (%) C,75.99; H,10.15; N,4.35; S,9.50.

REFERENTIAL EXAMPLE 6

To a mixture of 4.85 g (17.3 mmol) of 3,7-dimethyl-1-(4-methylphenyl)sulfonyl-2(E), 6-octadiene, 50 ml of anhydrous tetrahydrofuran, and 10 ml of anhydrous hexamethylphosphoric triamide is dropwise added 11 ml of a solution of 1.6M n-butyl lithium in hexane with stirring at −70°~−60° C. with cooling under nitrogen gas flow within 5 minutes. The mixture is stirred at the same temperature for 30 minutes, and mixed with a solution of 6.14 g (19 mmol) of 1-benzyloxy-8-bromo-3,7-dimethyl-2(E),6(E)-octadiene in 10 ml of anhydrous tetrahydrofuran. The mixture is stirred at the same temperature for 30 minutes then without cooling bath for about 1 hour. The reaction mixture is mixed with 10 ml of water, extracted with a mixture of Et$_2$O:hexane (1:1), washed twice with 100 ml of water, dried over anhydrous sodium sulfate, and evaporated. The residue is purified by silica-gel column chromatography and eluted with Et$_2$O:hexane (1:3) to give 6.0 g (yield: 66.3%) of 1-benzyloxy-9-(4-methyl)phenylsulfonyl-3,7,11, 15-tetramethyl-2(E),6(E),7(E),14-hexadecatetraene as colorless oil.

To a mixture of 6.0 g of the compound provided above, 10 ml of anhydrous tetrahydrofuran, and 50 ml of ethylamine is portionwise added 1.28 g of metal lithium at −30° C. for about 30 minutes. The mixture is stirred at the same temperature for about 2 hours.

After the color of the reaction mixture is turned from deep blue to pale yellow, 5 g of ammonium chloride is added gradually to the mixture. The resulting mixture is stirred at room temperature for 30 minutes, mixed with 150 ml of water, and extracted with 100 ml of a mixture of Et$_2$O:hexane (1:1). The organic layer is washed twice with 100 ml of water, dried over anhydrous sodium sulfate, and evaporated. The residual oil is purified by silica-gel column chromatography and eluted with Et$_2$O: hexane (1:2) to give 1.96 g of [E,E, E]-tetraprenol. Yield: 58.8%

REFERENTIAL EXAMPLES 7-9

[Z,E,E]-tetraprenol, [E,E,Z]-tetraprenol, and [Z,E,Z]-tetraprenol are prepared in the same manner as in Referential Example 6.

REFERENTIAL EXAMPLE 10

[Z,Z,Z]-Geranylgeraniol

To a stirred mixture of 5.92 g (10 mmol) of 6-benzyloxy-4-methyl-4(Z)-hexen-1-yl-triphenylphosphonium iodide in 50 ml of anhydrous tetrahydrofuran is added 1.39 g (12 mmol) of potassium tert-butoxide with ice-cooling with stirring under nitrogen gas flow.

The mixture is stirred at 20°±2° C. for 2 hours. To the mixture is dropwise added a solution of 1.94 g (10 mmol) of nerylacetone in 5 ml of anhydrous tetrahydrofuran under ice-cooling. The resulting mixture is stirred at the same temperature for 1 hour and at room temperature for another 3 hours. The reaction mixture is filtered and the filtrate is concentrated under reduced pressure. The residue is extracted with 100 ml of a mixture of Et$_2$O:hexane (1:1), washed twice with 100 ml of water, dried over anhydrous sodium sulfate, and evaporated. The resulting residue is purified by silica-gel column chromatography and eluted with Et$_2$O:hexane (1:2) to give 2.71 g of [Z,Z,Z]-geranylgeraniol benzyl ether as colorless liquid.

A mixture of 2.71 g of the compound provided above, 5 ml of anhydrous tetrahydrofuran, and 30 ml of ethylamine is treated with 600 mg of metal lithium in the same manner as in Referential Example 6 to give 1.84 g of [Z,Z,Z]-tetraprenol.

REFERENTIAL EXAMPLES 11-13

[Z,Z,E]-geranyl linalool, [E,Z,Z]-geranyl linalool, and [E,Z,E]-geranyl geraniol are prepared in the same manner as in Referential Example 10.

In Referential Examples 10-13, NaH/dimethylsulfoxide or hexamethylphosphoric triamide (10:1) can be used.

$^{13}$C-NMR Data of each of stereoisomers of a tetraprenol will be summarized in Table 15.

TABLE 15

The $^{13}$C-NMR Chemical Shift Data [δ (CDCl$_3$)ppm] of Each Stereoisomers of Tetraprenol (25.2 MHz, TMS Internal Standard)

HO-C1=C2-C3(C4)-C5-C6=C7-C8(C17)-C9-C10=C11-C12(C18)-C13-C14=C15(C16)-C16 (structural diagram with positions 1-16)

| | E,E,E | Z,E,E | E,E,Z | Z,E,Z | Z,Z,Z | Z,Z,E | E,Z,Z | E,Z,E |
|---|---|---|---|---|---|---|---|---|
| C$_1$ | 59.35 | 59.04 | 59.41 | 59.05 | 59.04 | 59.02 | 59.42 | 59.42 |
| C$_{16}$ | 25.69 | 25.69 | 25.71 | 25.72 | 25.72 | 25.69 | 25.70 | 25.69 |
| C$_{20}$ | 17.68 | 17.68 | 17.64 | 17.64 | 17.66 | 17.69 | 17.64 | 17.69 |
| C$_2$,C$_6$,C$_{10}$,C$_{14}$ | 124.46 / 124.25 / 123.87 / 123.49 | 124.50 / 124.46 / 124.15 / 123.65 | 125.05 / 124.44 / 123.86 / 123.47 | 124.97 / 124.50 / 124.44 / 123.67 | 124.89 / 124.54 / 124.48 / 124.40 | 124.50 / 124.45 / 124.14 / 124.39 | 125.09 / 125.03 / 124.64 / 124.39 | 124.58 / 124.42 / 124.15 / 123.55 |
| C$_3$ | 139.62 | 139.93 | 139.78 | 139.92 | 139.86 | 139.81 | 139.74 | 139.73 |
| C$_7$,C$_{11}$ | 135.38 / 134.97 | 135.99 / 135.08 | 135.39 / 135.14 | 135.93 / 135.21 | 136.11 / 135.47 | 136.21 / 135.13 | 135.50 / 135.31 | 135.59 / 135.22 |
| C$_{15}$ | 131.23 | 131.25 | 131.51 | 131.49 | 131.57 | 131.30 | 131.52 | 131.30 |
| C$_5$,C$_9$,C$_{13}$ | 26.82 / 26.68 / 26.40 | 26.82 / 26.59 | 26.66 / 26.57 / 26.37 | 26.67 / 26.59 / 26.52 | 26.68 / 26.42 / 26.34 | 26.77 / 26.61 / 26.39 | 26.71 / 26.39 / 26.24 | 26.77 / 26.55 / 26.24 |
| C$_4$, C$_8$, C$_{12}$ | 39.75 / 39.62 | 32.05 / 39.74 / 39.74 | 40.02 / 39.59 / 32.03 | 32.04 / 40.03 / 32.04 | 32.25 / 31.99 | 32.29 / 31.96 / 39.76 | 40.00 / 32.29 / 32.01 | (39.86) / 31.99 / (39.76) |
| C$_{17}$ | | 23.45 | 16.29 | (23.45) | | 23.44 | 16.28 | (16.29) |
| C$_{18}$, C$_{19}$ | 16.29 / 16.02 | 16.02 / 16.02 | 16.02 / 23.39 | 16.01 / (23.39) | 23.46 / 23.40 | 23.44 / 16.00 | 23.41 / 23.41 | 23.41 / (16.00) |

(Unassignable signals are shown in parentheses)

| Preparation | |
|---|---|
| Compound I-47 or Compound X II-5 | 10 mg |
| Lactose | 100 mg |
| Myclocrystalline cellulose | 30 mg |
| Gelatin | 5 mg |
| Magnesium stearate | 5 mg |
| | 150 mg |

The components described above are mixed with each other to give a tablet.

EFFECT

Experiment 1

Method

Male SD rats, weighing 200-300 g, were allowed to fast for 24 hours. One milliliter of 60% ethanol (v/v) in 150 mM hydrochloric acid was given orally 1 hour after oral or intraperitoneal administration of test compound as a suspension in 5% gum arabic, and the animals were killed with an overdose of ether 1 hour later. The stomachs were removed and opened along the greater curvature. The total length (mm) of each lesion was measured for use as the lesion index and inhibition (%) of lesion formation by the test compound was calculated by comparing with that of 5% gum arabic as control.

Result

The number of the test compounds corresponds to the compound number used in Examples.

Geranylgeranylacetone (hereinafter abbreviated as GGA) was employed as a reference compound.

| Compd. Nos. | Dose (mg/kg) | Inhibition (%) |
|---|---|---|
| Intraperitoneal administration | | |
| I-21 | 20 | 99.0 |
| I-20 | 20 | 83.1 |
| I-30 | 20 | 93.6 |
| I-22 | 20 | 85.6 |
| I-59 | 20 | 53.3 |
| I-65 | 20 | 35.5 |
| I-9 | 20 | 64.2 |
| I-2 | 10 | 71.7 |
| I-55 | 10 | 76.7 |
| I-57 | 20 | 84.0 |
| I-28 | 20 | 80.4 |
| I-13 | 20 | 65.3 |
| I-36 | 20 | 72.2 |
| I-18 | 20 | 75.1 |
| I-62 | 20 | 46.1 |
| I-71 | 20 | 68.5 |
| I-4 | 20 | 88.4 |
| I-12 | 10 | 39.4 |
| I-81 | 20 | 78.2 |
| I-24 | 10 | 62.1 |
| I-26 | 10 | 59.1 |
| I-31 | 20 | 91.0 |
| I-29 | 10 | 64.3 |
| I-56 | 20 | 79.4 |
| I-82 | 20 | 62.7 |
| GGA | 50 | 81.0 |
| Oral administration | | |
| I-21 | 20 | 64.5 |
| I-20 | 20 | 24.2 |
| I-30 | 20 | 85.1 |
| I-22 | 20 | 86.1 |
| I-2 | 20 | 46.6 |
| I-55 | 10 | 22.2 |
| I-57 | 10 | 36.2 |
| I-36 | 20 | 56.4 |
| I-71 | 20 | 44.2 |
| I-4 | 20 | 29.3 |
| I-81 | 20 | 23.9 |
| I-24 | 20 | 11.8 |
| I-26 | 20 | 9.6 |
| GGA | 20 | 37.7 |

Experiment 2

Method

Male Jcl SD rats (body weight; about 300 g) were allowed to fast for 24 hours and anesthetized by urethane. Cannula was put into the trachea and into a jugular vein. After midline laparotomy, perfusion cannulae were introduced into the stomach through the pylorus and the esophagus. The animal was perfused with saline (1 ml/min) at 37° C. through the esophagus cannula. Perfusate was collected every 15 minutes through the pylorus cannula and titrated with 0.01N sodium hydroxide to measure acid secretion. Histamine dihydrochloride (3 mg/kg/hr) was infused through the jugular vein cannula and the test compound was administered intraduodenaly 90 minutes later. Acid output in perfusate every 15 minutes was measured in the same manner as described above. The rate of maximum inhibition (%) of acid secretion was calculated during 90 minutes after administration of the test compound compared with the acid output just before administration of the test compound.

| Compd. Nos. | Dose (mg/kg) | Inhibition (%) |
|---|---|---|
| I-30 | 20 | 57.4 |
|  | 50 | 99.5 |
| I-55 | 20 | 51.1 |
|  | 50 | 77.7 |

What we claim is:

1. A compound of the formula:

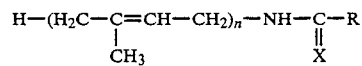

wherein n is an integer of 1 to 6;

R is amino or amino substituted by a member selected from the group consisting of

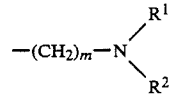

wherein m=2-5, and $R^1$ and $R^2$ are each $C_1$-$C_5$ alkyl, phenyl($C_1$-$C_5$ alkyl), halogenophenyl($C_1$-$C_5$ alkyl), 3,4-methylenedioxypenyl ($C_1$-$C_5$ alkyl), morpholinyl($C_1$-$C_5$ alkyl), pyridyl-$C_1$-$C_5$ alkyl, phenyl, halogenophenyl, trifluoromethylphenyl, $C_1$-$C_5$ alkoxyphenyl, pyridyl, $C_1$-$C_5$ alkyl, and di($C_1$-$C_5$ alkyl);

X is sulfur or oxygen; or an acid addition salt thereof.

2. The compound claimed in claim 1, namely N-(3,7,11,15-tetramethyl-2,6,10,14-hexadecatetraenyl)urea.

3. The compound claimed in claim 1, namely N-(3,7,11,15-tetramethyl-2,6,10,14-hexadecatetraenyl)-N'-dimethylaminoethylurea.

4. The compound claimed in claim 1, namely N-(3,7,11,15-tetramethyl-2,6,10,14-hexadecatetraenyl)-N'-(2-pyridyl)urea.

5. The compound claimed in claim 1, namely N-(3,7,11,15-tetramethyl-2,6,10,14-hexadecatetraenyl)-N'-(3-pyridyl)urea.

6. The compound claimed in claim 1, namely N-(3,7,11,15-tetramethyl-2,6,10,14-hexadecatetraenyl)-N'-(4-pyridyl)urea.

7. The compound claimed in claim 1, namely N-(3,7,11,15-tetramethyl-2,6,10,14-hexadecatetraenyl)-N'-(2-pyridylmethyl)urea.

8. The compound claimed in claim 1, namely N-(3,7,11,15-tetramethyl-2,6,10,14-hexadecatetraenyl)-N'-(3-pyridylmethyl)urea.

9. The compound claimed in claim 1, namely N-(3,7,11,15-tetramethyl-2,6,10,14-hexadecatetraenyl)-N'-(4-pyridylmethyl)urea.

10. The compound claimed in claim 1, namely N-(3,7,11,15-tetramethyl-2,6,10,14-hexadecatetraenyl)-N'-(2-pyridylethyl)urea.

11. The compound claimed in claim 1, namely N-(3,7,11,15-tetramethyl-2,6,10,14-hexadecatetraenyl)-N'-(3-pyridylethyl)urea.

12. The compound claimed in claim 1, namely N-(3,7,11,15-tetramethyl-2,6,10,14-hexadecatetraenyl)-N'-(4-pyridylethyl)urea.

13. An antiulcer composition comprising a pharmaceutically effective amount of a compound according to claim 1 for treating ulcers and a suitable carrier therefor.

14. A method for treating an ulcer, which comprises, administering to a patient a pharmaceutically effective amount of the antiulcer composition of claim 13.

15. The method according to claim 14, wherein the mode of administering is oral or parenteral.

16. The method according to claim 14, wherein about 1 to 500 mg/kg of said compound is administered to the patient.

* * * * *